(12) United States Patent
Van Niekerk et al.

(10) Patent No.: US 12,714,497 B2
(45) Date of Patent: Aug. 25, 2026

(54) BASKET CATHETER DISTAL END FEATURE

(71) Applicant: Biosense Webster (Israel) Ltd., Yokneam (IL)

(72) Inventors: Pieter Emmelius Van Niekerk, Rancho Santa Margarita, CA (US); William James Agnew, V, Rancho Santa Margarita, CA (US); Sean D. Thaler, Rancho Cucamonga, CA (US); Jasson Rodriguez, Irvine, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 226 days.

(21) Appl. No.: 18/650,737

(22) Filed: Apr. 30, 2024

(65) Prior Publication Data

US 2024/0398468 A1 Dec. 5, 2024

Related U.S. Application Data

(60) Provisional application No. 63/505,978, filed on Jun. 2, 2023.

(51) Int. Cl.
*A61B 18/14* (2006.01)
*A61B 18/00* (2006.01)

(52) U.S. Cl.
CPC .. *A61B 18/1492* (2013.01); *A61B 2018/0016* (2013.01); *A61B 2018/00172* (2013.01);
(Continued)

(58) Field of Classification Search
CPC ...... A61B 2018/144; A61B 2018/1407; A61B 2018/00267; A61B 2018/141;
(Continued)

(56) References Cited

U.S. PATENT DOCUMENTS 4,699,147 A 10/1987 Chilson et al.
4,940,064 A 7/1990 Desai
(Continued)

FOREIGN PATENT DOCUMENTS

CN 111248993 A 6/2020
CN 111248996 A 6/2020
(Continued)

OTHER PUBLICATIONS

Extended European Search Report and Opinion dated Jan. 13, 2025, from corresponding European Application No. 24179164.9.

*Primary Examiner* — Joseph A Stoklosa
*Assistant Examiner* — Marina Delaney Templeton

(57) ABSTRACT

A catheter having an end effector with multiple spines forming a basket shape is disclosed herein. The end effector can include spine loops with overlapping extensions at a distal end of the end effector. The end effector can include one or more inflatable members that are deflated during delivery and inflate to prevent the distal end of the basket assembly from contacting tissue. The end effector can include a spine hub at a distal end of the basket assembly with spine loops that extend through openings of the spine hub. The end effector can include a spiral inductor at the distal end of the basket assembly. The end effector can include an atraumatic structure over a distal end of a frame of the basket assembly.

19 Claims, 10 Drawing Sheets

(52) U.S. Cl.
CPC ............... *A61B 2018/00267* (2013.01); *A61B 2018/00351* (2013.01); *A61B 2018/00577* (2013.01); *A61B 2018/00839* (2013.01); *A61B 2018/1467* (2013.01); *A61B 2018/1475* (2013.01)

(58) Field of Classification Search
CPC .......... A61B 2018/00278; A61B 2018/00613; A61B 2018/0022; A61B 2018/00214; A61B 2018/1475; A61B 2018/1467; A61B 2018/00839; A61B 2018/00577; A61B 2018/00351; A61B 2018/00172; A61B 17/221; A61B 5/6858; A61B 5/6859; A61B 5/6856; A61B 5/333; A61B 5/318; A61B 5/367; A61B 5/283; A61B 18/12; A61B 18/1206; A61B 2017/00053; A61B 2017/00039; A61N 1/3629
See application file for complete search history.

(56) References Cited

U.S. PATENT DOCUMENTS 5,215,103 A 6/1993 Desai
5,255,679 A 10/1993 Imran
5,293,869 A 3/1994 Edwards et al.
5,309,910 A 5/1994 Edwards et al.
5,313,943 A 5/1994 Houser et al.
5,324,284 A 6/1994 Imran
5,345,936 A 9/1994 Pomeranz et al.
5,365,926 A 11/1994 Desai
5,391,199 A 2/1995 Ben-Haim
5,396,887 A 3/1995 Imran
5,400,783 A 3/1995 Pomeranz et al.
5,411,025 A 5/1995 Webster, Jr.
5,415,166 A 5/1995 Imran
5,443,489 A 8/1995 Ben-Haim
5,456,254 A 10/1995 Pietroski et al.
5,465,717 A 11/1995 Imran et al.
5,476,495 A 12/1995 Kordis et al.
5,499,981 A 3/1996 Kordis
5,526,810 A 6/1996 Wang
5,546,940 A 8/1996 Panescu et al.
5,549,108 A 8/1996 Edwards et al.
5,558,073 A 9/1996 Pomeranz et al.
5,558,091 A 9/1996 Acker et al.
5,577,509 A 11/1996 Panescu et al.
5,595,183 A 1/1997 Swanson et al.
5,598,848 A 2/1997 Swanson et al.
5,609,157 A 3/1997 Panescu et al.
5,628,313 A 5/1997 Webster, Jr.
5,681,280 A 10/1997 Rusk et al.
5,722,401 A 3/1998 Pietroski et al.
5,722,403 A 3/1998 McGee et al.
5,725,525 A 3/1998 Kordis
5,730,128 A 3/1998 Pomeranz et al.
5,772,590 A 6/1998 Webster, Jr.
5,782,840 A * 7/1998 Nakao .................... A61B 18/14 606/113
5,782,899 A 7/1998 Imran
5,800,482 A * 9/1998 Pomeranz ............. A61N 1/056 606/41
5,823,189 A 10/1998 Kordis
5,881,727 A 3/1999 Edwards
5,893,847 A 4/1999 Kordis
5,904,680 A 5/1999 Kordis et al.
5,911,739 A 6/1999 Kordis et al.
5,928,228 A 7/1999 Kordis et al.
5,968,040 A 10/1999 Swanson et al.
5,989,266 A * 11/1999 Foster ................. A61B 17/221 606/127
6,014,579 A 1/2000 Pomeranz et al.
6,014,590 A 1/2000 Whayne et al.
6,119,030 A 9/2000 Morency
6,172,499 B1 1/2001 Ashe
6,216,043 B1 4/2001 Swanson et al.
6,216,044 B1 4/2001 Kordis
6,239,724 B1 5/2001 Doron et al.
6,332,089 B1 12/2001 Acker et al.
6,428,537 B1 8/2002 Swanson et al.
6,456,864 B1 9/2002 Swanson et al.
6,484,118 B1 11/2002 Govari
6,574,492 B1 6/2003 Ben-Haim et al.
6,584,345 B2 6/2003 Govari
6,600,948 B2 7/2003 Ben-Haim et al.
6,618,612 B1 9/2003 Acker et al.
6,690,963 B2 2/2004 Ben-Haim et al.
6,738,655 B1 5/2004 Sen et al.
6,741,878 B2 5/2004 Fuimaono et al.
6,748,255 B2 6/2004 Fuimaono et al.
6,780,183 B2 8/2004 Jimenez, Jr. et al.
6,788,967 B2 9/2004 Ben-Haim et al.
6,837,886 B2 1/2005 Collins et al.
6,866,662 B2 3/2005 Fuimaono et al.
6,892,091 B1 5/2005 Ben-Haim et al.
6,970,730 B2 11/2005 Fuimaono et al.
6,973,340 B2 12/2005 Fuimaono et al.
6,980,858 B2 12/2005 Fuimaono et al.
7,048,734 B1 5/2006 Fleischman et al.
7,149,563 B2 12/2006 Fuimaono et al.
7,255,695 B2 8/2007 Falwell et al.
7,257,434 B2 8/2007 Fuimaono et al.
7,399,299 B2 7/2008 Daniel et al.
7,410,486 B2 8/2008 Fuimaono et al.
7,522,950 B2 4/2009 Fuimaono et al.
7,536,218 B2 5/2009 Govari et al.
RE41,334 E 5/2010 Beatty et al.
7,756,576 B2 7/2010 Levin
7,846,157 B2 12/2010 Kozel
7,848,787 B2 12/2010 Osadchy
7,869,865 B2 1/2011 Govari et al.
7,930,018 B2 4/2011 Harlev et al.
8,007,495 B2 8/2011 McDaniel et al.
8,048,063 B2 11/2011 Aeby et al.
8,103,327 B2 1/2012 Harlev et al.
8,167,845 B2 5/2012 Wang et al.
8,224,416 B2 7/2012 De La Rama et al.
8,235,988 B2 8/2012 Davis et al.
8,346,339 B2 1/2013 Kordis et al.
8,435,232 B2 5/2013 Aeby et al.
8,447,377 B2 5/2013 Harlev et al.
8,456,182 B2 6/2013 Bar-Tal et al.
8,498,686 B2 7/2013 Grunewald
8,517,999 B2 8/2013 Pappone et al.
8,545,490 B2 10/2013 Mihajlovic et al.
8,560,086 B2 10/2013 Just et al.
8,567,265 B2 10/2013 Aeby et al.
8,712,550 B2 4/2014 Grunewald
8,755,861 B2 6/2014 Harlev et al.
8,825,130 B2 9/2014 Just et al.
8,906,011 B2 12/2014 Gelbart et al.
8,945,120 B2 2/2015 McDaniel et al.
8,979,839 B2 3/2015 De La Rama et al.
9,037,264 B2 5/2015 Just et al.
9,131,980 B2 9/2015 Bloom
9,204,929 B2 12/2015 Solis
9,277,960 B2 3/2016 Weinkam et al.
9,314,208 B1 4/2016 Altmann et al.
9,339,331 B2 5/2016 Tegg et al.
9,486,282 B2 11/2016 Solis
9,554,718 B2 1/2017 Bar-Tal et al.
D782,686 S 3/2017 Werneth et al.
9,585,588 B2 3/2017 Marecki et al.
9,597,036 B2 3/2017 Aeby et al.
9,687,297 B2 6/2017 Just et al.
9,693,733 B2 7/2017 Altmann et al.
9,782,099 B2 10/2017 Williams et al.
9,788,895 B2 10/2017 Solis
9,801,681 B2 10/2017 Laske et al.
9,814,618 B2 11/2017 Nguyen et al.
9,833,161 B2 12/2017 Govari
9,894,756 B2 2/2018 Weinkam et al.
9,895,073 B2 2/2018 Solis
9,907,609 B2 3/2018 Cao et al.

(56) References Cited

U.S. PATENT DOCUMENTS 9,974,460 B2 5/2018 Wu et al.
9,986,949 B2 6/2018 Govari et al.
9,993,160 B2 6/2018 Salvestro et al.
10,014,607 B1 7/2018 Govari et al.
10,028,376 B2 7/2018 Weinkam et al.
10,034,637 B2 7/2018 Harlev et al.
10,039,494 B2 8/2018 Altmann et al.
10,045,707 B2 8/2018 Govari
10,078,713 B2 9/2018 Auerbach et al.
10,111,623 B2 10/2018 Jung et al.
10,130,420 B2 11/2018 Basu et al.
10,136,828 B2 11/2018 Houben et al.
10,143,394 B2 12/2018 Solis
10,172,536 B2 1/2019 Maskara et al.
10,182,762 B2 1/2019 Just et al.
10,194,818 B2 2/2019 Williams et al.
10,201,311 B2 2/2019 Chou et al.
10,219,860 B2 3/2019 Harlev et al.
10,219,861 B2 3/2019 Just et al.
10,231,328 B2 3/2019 Weinkam et al.
10,238,309 B2 3/2019 Bar-Tal et al.
10,278,590 B2 5/2019 Salvestro et al.
D851,774 S 6/2019 Werneth et al.
10,314,505 B2 6/2019 Williams et al.
10,314,507 B2 6/2019 Govari et al.
10,314,648 B2 6/2019 Ge et al.
10,314,649 B2 6/2019 Bakos et al.
10,349,855 B2 7/2019 Zeidan et al.
10,350,003 B2 7/2019 Weinkam et al.
10,362,991 B2 7/2019 Tran et al.
10,375,827 B2 8/2019 Weinkam et al.
10,376,170 B2 8/2019 Quinn et al.
10,376,221 B2 8/2019 Iyun et al.
10,398,348 B2 9/2019 Osadchy et al.
10,403,053 B2 9/2019 Katz et al.
10,441,188 B2 10/2019 Katz et al.
10,470,682 B2 11/2019 Deno et al.
10,470,714 B2 11/2019 Altmann et al.
10,482,198 B2 11/2019 Auerbach et al.
10,492,857 B2 12/2019 Guggenberger et al.
10,542,620 B2 1/2020 Weinkam et al.
10,575,743 B2 3/2020 Basu et al.
10,575,745 B2 3/2020 Solis
10,582,871 B2 3/2020 Williams et al.
10,582,894 B2 3/2020 Ben Zrihem et al.
10,596,346 B2 3/2020 Aeby et al.
10,602,947 B2 3/2020 Govari et al.
10,617,867 B2 4/2020 Viswanathan et al.
10,660,702 B2 5/2020 Viswanathan et al.
10,667,753 B2 6/2020 Werneth et al.
10,674,929 B2 6/2020 Houben et al.
10,681,805 B2 6/2020 Weinkam et al.
10,682,181 B2 6/2020 Cohen et al.
10,687,892 B2 6/2020 Long et al.
10,702,178 B2 7/2020 Dahlen et al.
10,716,477 B2 7/2020 Salvestro et al.
10,758,304 B2 9/2020 Aujla
10,765,371 B2 9/2020 Hayam et al.
10,772,566 B2 9/2020 Aujila
10,799,281 B2 10/2020 Goertzen et al.
10,842,558 B2 11/2020 Harlev et al.
10,842,561 B2 11/2020 Viswanathan et al.
10,863,914 B2 12/2020 Govari et al.
10,881,376 B2 1/2021 Shemesh et al.
10,898,139 B2 1/2021 Guta et al.
10,905,329 B2 2/2021 Bar-Tal et al.
10,912,484 B2 2/2021 Ziv-Ari et al.
10,918,306 B2 2/2021 Govari et al.
10,939,871 B2 3/2021 Altmann et al.
10,952,795 B2 3/2021 Cohen et al.
10,973,426 B2 4/2021 Williams et al.
10,973,461 B2 4/2021 Baram et al.
10,987,045 B2 4/2021 Basu et al.
11,006,902 B1 5/2021 Bonyak et al.
11,040,208 B1 6/2021 Govari et al.
11,045,628 B2 6/2021 Beeckler et al.
11,051,877 B2 7/2021 Sliwa et al.
11,109,788 B2 9/2021 Rottmann et al.
11,116,435 B2 9/2021 Urman et al.
11,129,574 B2 9/2021 Cohen et al.
11,160,482 B2 11/2021 Solis
11,164,371 B2 11/2021 Yellin et al.
2002/0068897 A1* 6/2002 Jenkins .............. A61B 18/1492 604/96.01
2004/0122444 A1* 6/2004 Gerard ................ A61B 17/221 606/127
2004/0210121 A1 10/2004 Fuimaono et al.
2006/0009689 A1 1/2006 Fuimaono et al.
2006/0009690 A1 1/2006 Fuimaono et al.
2006/0100669 A1 5/2006 Fuimaono et al.
2007/0093806 A1 4/2007 Desai et al.
2007/0276212 A1 11/2007 Fuimaono et al.
2008/0234564 A1 9/2008 Beatty et al.
2011/0118726 A1 5/2011 De La Rama et al.
2011/0160574 A1 6/2011 Harlev et al.
2011/0190625 A1 8/2011 Harlev et al.
2011/0245756 A1 10/2011 Arora et al.
2011/0301597 A1 12/2011 McDaniel et al.
2012/0271140 A1* 10/2012 Kordis ................... A61B 5/283 600/375
2013/0172872 A1 7/2013 Subramaniam et al.
2013/0172883 A1 7/2013 Lopes et al.
2013/0178850 A1 7/2013 Lopes et al.
2013/0190587 A1 7/2013 Lopes et al.
2013/0296852 A1 11/2013 Madjarov et al.
2014/0025069 A1 1/2014 Willard et al.
2014/0052118 A1 2/2014 Laske et al.
2014/0180147 A1 6/2014 Thakur et al.
2014/0180151 A1 6/2014 Maskara et al.
2014/0180152 A1 6/2014 Maskara et al.
2014/0257069 A1 9/2014 Eliason et al.
2014/0276712 A1 9/2014 Mallin et al.
2014/0309512 A1 10/2014 Govari et al.
2015/0011991 A1 1/2015 Buysman et al.
2015/0045863 A1 2/2015 Litscher et al.
2015/0080693 A1 3/2015 Solis
2015/0105770 A1 4/2015 Amit
2015/0119878 A1 4/2015 Heisel et al.
2015/0133919 A1 5/2015 McDaniel et al.
2015/0208942 A1 7/2015 Bar-Tal et al.
2015/0250424 A1 9/2015 Govari et al.
2015/0270634 A1 9/2015 Buesseler et al.
2015/0342532 A1 12/2015 Basu et al.
2016/0081746 A1 3/2016 Solis
2016/0113582 A1 4/2016 Altmann et al.
2016/0113709 A1 4/2016 Maor
2016/0183877 A1 6/2016 Williams et al.
2016/0228023 A1 8/2016 Govari
2016/0228062 A1 8/2016 Altmann et al.
2016/0278853 A1 9/2016 Ogle et al.
2016/0302858 A1 10/2016 Bencini
2016/0338770 A1 11/2016 Bar-Tal et al.
2017/0027638 A1 2/2017 Solis
2017/0065227 A1 3/2017 Marrs et al.
2017/0071543 A1 3/2017 Basu et al.
2017/0071544 A1 3/2017 Basu et al.
2017/0071665 A1 3/2017 Solis
2017/0095173 A1 4/2017 Bar-Tal et al.
2017/0100187 A1 4/2017 Basu et al.
2017/0143227 A1 5/2017 Marecki et al.
2017/0156790 A1 6/2017 Aujla
2017/0172442 A1 6/2017 Govari
2017/0185702 A1 6/2017 Auerbach et al.
2017/0202515 A1 7/2017 Zrihem et al.
2017/0221262 A1 8/2017 Laughner et al.
2017/0224958 A1 8/2017 Cummings et al.
2017/0265812 A1 9/2017 Williams et al.
2017/0281031 A1 10/2017 Houben et al.
2017/0281268 A1 10/2017 Tran et al.
2017/0296125 A1 10/2017 Altmann et al.
2017/0296251 A1 10/2017 Wu et al.
2017/0347959 A1 12/2017 Guta et al.
2017/0354338 A1 12/2017 Levin et al.
2017/0354339 A1 12/2017 Zeidan et al.

(56) References Cited

U.S. PATENT DOCUMENTS

2017/0354364 A1 12/2017 Bar-Tal et al.
2018/0008203 A1 1/2018 Iyun et al.
2018/0028084 A1 2/2018 Williams et al.
2018/0049803 A1 2/2018 Solis
2018/0085064 A1 3/2018 Auerbach et al.
2018/0132749 A1 5/2018 Govari et al.
2018/0137687 A1 5/2018 Katz et al.
2018/0160936 A1 6/2018 Govari et al.
2018/0160978 A1 6/2018 Cohen et al.
2018/0168511 A1 6/2018 Hall et al.
2018/0184982 A1 7/2018 Basu et al.
2018/0192958 A1 7/2018 Wu
2018/0206792 A1 7/2018 Auerbach et al.
2018/0235692 A1 8/2018 Efimov et al.
2018/0249959 A1 9/2018 Osypka
2018/0256109 A1 9/2018 Wu et al.
2018/0279954 A1 10/2018 Hayam et al.
2018/0303414 A1 10/2018 Toth et al.
2018/0310987 A1 11/2018 Altmann et al.
2018/0311497 A1 11/2018 Viswanathan et al.
2018/0338722 A1 11/2018 Altmann et al.
2018/0344188 A1 12/2018 Govari
2018/0344202 A1 12/2018 Bar-Tal et al.
2018/0344251 A1 12/2018 Harlev et al.
2018/0344393 A1 12/2018 Gruba et al.
2018/0360534 A1 12/2018 Teplitsky et al.
2018/0365355 A1 12/2018 Auerbach et al.
2019/0000540 A1 1/2019 Cohen et al.
2019/0008582 A1 1/2019 Govari et al.
2019/0015007 A1 1/2019 Rottmann et al.
2019/0030328 A1 1/2019 Stewart et al.
2019/0053708 A1 2/2019 Gliner
2019/0059766 A1 2/2019 Houben et al.
2019/0069950 A1 3/2019 Viswanathan et al.
2019/0069954 A1 3/2019 Cohen et al.
2019/0117111 A1 4/2019 Osadchy et al.
2019/0117303 A1 4/2019 Claude et al.
2019/0117315 A1 4/2019 Keyes et al.
2019/0125439 A1 5/2019 Rohl et al.
2019/0133552 A1 5/2019 Shemesh et al.
2019/0142293 A1 5/2019 Solis
2019/0164633 A1 5/2019 Ingel et al.
2019/0167137 A1 6/2019 Bar-Tal et al.
2019/0167140 A1 6/2019 Williams et al.
2019/0188909 A1 6/2019 Yellin et al.
2019/0201664 A1 7/2019 Govari
2019/0209089 A1 7/2019 Baram et al.
2019/0216346 A1 7/2019 Ghodrati et al.
2019/0216347 A1 7/2019 Ghodrati et al.
2019/0231421 A1 8/2019 Viswanathan et al.
2019/0231423 A1 8/2019 Weinkam et al.
2019/0239811 A1 8/2019 Just et al.
2019/0246935 A1 8/2019 Govari et al.
2019/0298442 A1 10/2019 Ogata et al.
2019/0314083 A1 10/2019 Herrera et al.
2019/0328260 A1 10/2019 Zeidan et al.
2019/0343580 A1 11/2019 Nguyen et al.
2020/0000518 A1 1/2020 Kiernan et al.
2020/0008705 A1 1/2020 Ziv-Ari et al.
2020/0008869 A1 1/2020 Byrd
2020/0009378 A1 1/2020 Stewart et al.
2020/0015890 A1 1/2020 To et al.
2020/0022653 A1 1/2020 Moisa
2020/0029845 A1 1/2020 Baram et al.
2020/0046421 A1 2/2020 Govari
2020/0046423 A1 2/2020 Mswanathan et al.
2020/0060569 A1 2/2020 Tegg
2020/0077959 A1 3/2020 Altmann et al.
2020/0093539 A1 3/2020 Long et al.
2020/0129089 A1 4/2020 Gliner et al.
2020/0129125 A1 4/2020 Govari et al.
2020/0129128 A1 4/2020 Gliner et al.
2020/0155224 A1 5/2020 Bar-Tal
2020/0179650 A1 6/2020 Beeckler et al.
2020/0196896 A1 6/2020 Solis
2020/0205689 A1 7/2020 Squires et al.
2020/0205690 A1 7/2020 Williams et al.
2020/0205737 A1 7/2020 Beeckler
2020/0205876 A1 7/2020 Govari
2020/0205892 A1 7/2020 Viswanathan et al.
2020/0206461 A1 7/2020 Govari et al.
2020/0206498 A1 7/2020 Arora et al.
2020/0289197 A1 9/2020 Viswanathan et al.
2020/0297234 A1 9/2020 Houben et al.
2020/0297281 A1 9/2020 Basu et al.
2020/0305726 A1 10/2020 Salvestro et al.
2020/0305946 A1 10/2020 DeSimone et al.
2020/0397328 A1 12/2020 Altmann et al.
2020/0398048 A1 12/2020 Krimsky et al.
2021/0015549 A1 1/2021 Haghighi-Mood et al.
2021/0022684 A1 1/2021 Govari et al.
2021/0045805 A1 2/2021 Govari et al.
2021/0059549 A1 3/2021 Urman et al.
2021/0059550 A1 3/2021 Urman et al.
2021/0059608 A1 3/2021 Beeckler et al.
2021/0059743 A1 3/2021 Govari
2021/0059747 A1 3/2021 Krans et al.
2021/0077184 A1 3/2021 Basu et al.
2021/0082157 A1 3/2021 Rosenberg et al.
2021/0085200 A1 3/2021 Auerbach et al.
2021/0085204 A1 3/2021 Auerbach et al.
2021/0085215 A1 3/2021 Auerbach et al.
2021/0085387 A1 3/2021 Amit et al.
2021/0093292 A1 4/2021 Baram et al.
2021/0093294 A1 4/2021 Shemesh et al.
2021/0093374 A1 4/2021 Govari et al.
2021/0093377 A1 4/2021 Herrera et al.
2021/0100612 A1 4/2021 Baron et al.
2021/0113822 A1 4/2021 Beeckler et al.
2021/0127999 A1 5/2021 Govari et al.
2021/0128010 A1 5/2021 Govari et al.
2021/0133516 A1 5/2021 Govari et al.
2021/0145282 A1 5/2021 Bar-Tal et al.
2021/0161592 A1 6/2021 Altmann et al.
2021/0162210 A1 6/2021 Altmann et al.
2021/0169421 A1 6/2021 Govari
2021/0169550 A1 6/2021 Govari et al.
2021/0169567 A1 6/2021 Govari et al.
2021/0169568 A1 6/2021 Govari et al.
2021/0177294 A1 6/2021 Gliner et al.
2021/0177356 A1 6/2021 Gliner et al.
2021/0177503 A1 6/2021 Altmann et al.
2021/0178166 A1 6/2021 Govari et al.
2021/0186363 A1 6/2021 Gliner et al.
2021/0186604 A1 6/2021 Altmann et al.
2021/0187241 A1 6/2021 Govari et al.
2021/0196372 A1 7/2021 Altmann et al.
2021/0196394 A1 7/2021 Govari et al.
2021/0212591 A1 7/2021 Govari et al.
2021/0219904 A1 7/2021 Yarnitsky et al.
2021/0278936 A1 9/2021 Katz et al.
2021/0282659 A1 9/2021 Govari et al.
2021/0307815 A1 10/2021 Govari et al.
2021/0308424 A1 10/2021 Beeckler et al.
2021/0338319 A1 11/2021 Govari et al.
2021/0369339 A1 12/2021 Salazar et al.
2022/0361942 A1 11/2022 Lichter et al.

FOREIGN PATENT DOCUMENTS

EP 0668740 A1 8/1995
EP 0644738 B1 3/2000
EP 0727183 B1 11/2002
EP 0727184 B1 12/2002
EP 2783651 A1 10/2014
EP 2699151 B1 11/2015
EP 2699152 B1 11/2015
EP 2699153 B1 12/2015
EP 2498706 B1 4/2016
EP 2578173 B1 6/2017
EP 3238645 A1 11/2017
EP 2884931 B1 1/2018
EP 2349440 B1 8/2019
EP 3318211 B1 12/2019

(56) References Cited

FOREIGN PATENT DOCUMENTS

| | | | |
|---|---|---|---|
| EP | 3581135 | A1 | 12/2019 |
| EP | 2736434 | B1 | 2/2020 |
| EP | 3451962 | B1 | 3/2020 |
| EP | 3972510 | A1 | 3/2022 |
| EP | 4393434 | A1 | 7/2024 |
| WO | 9421167 | A1 | 9/1994 |
| WO | 9421169 | A1 | 9/1994 |
| WO | 9625095 | A1 | 8/1996 |
| WO | 9634560 | A1 | 11/1996 |
| WO | 0182814 | B1 | 5/2002 |
| WO | 2004087249 | A2 | 10/2004 |
| WO | 2012100185 | A2 | 7/2012 |
| WO | 2013052852 | A1 | 4/2013 |
| WO | 2013162884 | A1 | 10/2013 |
| WO | 2013173917 | A1 | 11/2013 |
| WO | 2013176881 | A1 | 11/2013 |
| WO | 2014176205 | A1 | 10/2014 |
| WO | 2016019760 | A1 | 2/2016 |
| WO | 2016044687 | A1 | 3/2016 |
| WO | 2018111600 | A1 | 6/2018 |
| WO | 2018191149 | A1 | 10/2018 |
| WO | 2019084442 | A1 | 5/2019 |
| WO | 2019143960 | A1 | 7/2019 |
| WO | 2020026217 | A1 | 2/2020 |
| WO | 2020206328 | A1 | 10/2020 |

* cited by examiner

BASKET CATHETER DISTAL END FEATURE

CROSS REFERENCE TO RELATED APPLICATIONS

The application claims benefit of priority to prior filed U.S. Provisional Patent Application No. 63/505,978 filed Jun. 2, 2023, which is hereby incorporated by reference in full herein.

BACKGROUND

Cardiac arrhythmias, such as atrial fibrillation (AF), occur when regions of cardiac tissue abnormally conduct electric signals to adjacent tissue. This disrupts the normal cardiac cycle and causes asynchronous rhythm. Certain procedures exist for treating arrhythmia, which are surgical, or catheter based and aimed at disrupting the origin of the signals causing the arrhythmia and disrupting the conducting pathway for such signals. This work is directed to catheter-based cardiac ablation medical devices, and in particular catheters having a basket shaped end effector with electrodes.

Many contemporaneous ablation approaches utilize radiofrequency (RF) electrical energy to heat tissue. RF ablation can have certain rare drawbacks due to operator's skill, such as heightened risk of thermal cell injury which can lead to tissue charring, burning, steam pop, phrenic nerve palsy, pulmonary vein stenosis, and esophageal fistula. Cryoablation is an alternative approach to RF ablation that can reduce some thermal risks associated with RF ablation but may present tissue damage due to the extremely low temperature nature of such devices. Maneuvering cryoablation devices and selectively applying cryoablation is generally more challenging compared to RF ablation; therefore, cryoablation is not viable in certain anatomical geometries which may be reached by electrical ablation devices. Ablation by irreversible electroporation (IRE) is a more recent nonthermal ablation method. To achieve IRE, short pulses of high voltage electrical signals are delivered to tissues and the electrical signals generate an unrecoverable permeabilization of cell membranes.

Regions of cardiac tissue can be mapped by a catheter to identify the abnormal electrical signals. Some catheter ablation procedures especially those with persistent atrial fibrillation, may be performed using electrophysiology (EP) mapping to target areas of aberrant electrical signals. Such EP mapping may include the use of sensing electrodes configured to monitor electrical signals within the cardiovascular system to pinpoint the location of aberrant conductive tissue sites that are responsible for the arrhythmia.

In addition to using EP mapping, some catheter ablation procedures may be performed using an image guided surgery (IGS) system. The IGS system may enable the physician to visually track the location of the catheter within the patient, in relation to images of anatomical structures within the patient, in real time. Some systems may provide a combination of EP mapping and IGS functionalities, including the CARTO 3® system by Biosense Webster, Inc. of Irvine, Calif.

The same or different catheter can be used to perform ablation. There are presently a variety of multi-electrode end effector designs for these purposes. One category of end effectors, referred to herein as a basket catheter, includes a plurality of resilient spines joined at a distal end and a proximal end that expand to form a spheroid or ovate spheroid shape. The spines carry and/or include electrodes that can be configured for sensing and/or ablation.

SUMMARY

A catheter having an end effector with multiple spines forming a basket shape is disclosed herein. A distal portion of the end effector includes structures to provide an atraumatic surface, join the spines, and/or provide a location sensor.

An exemplary end effector of a medical probe can include a plurality of spines, a first loop member, a second loop member, and one or more electrodes. The plurality of spines can extend along a longitudinal axis and can be configured to expand away from the longitudinal axis to form a basket shape. The first loop member can include a first pair of spines of the plurality of spines and a first central region disposed approximate a distal end of the end effector. The second loop member can include a second pair of spines of the plurality of spines and a second central region disposed approximate the distal end of the end effector, the second central region comprising a portion disposed over a distal surface of the first central region and at least one extension disposed under a proximal surface of the first central region. The one or more electrodes can be coupled to each spine of the plurality of spines.

Another exemplary end effector of a medical probe can include a plurality of spines, a plurality of inflatable members, and one or more electrodes. The plurality of spines can extend along a longitudinal axis and can be configured to expand away from the longitudinal axis to form a basket shape. The plurality of inflatable members can each be coupled to a respective spine of the plurality of spines approximate a distal end of the end effector. The plurality of inflatable members can be configured to collapse for delivery through a sheath. The plurality of inflatable members can be configured to inflate in a deployed configuration. In the deployed configuration, the plurality of inflatable members can prevent a distal end of the basket shape of the plurality of spines from contacting tissue. The one or more electrodes can be coupled to each spine of the plurality of spines.

Another exemplary end effector of a medical probe can include a plurality of spines, a first loop member, a second loop member, and one or more electrodes. The plurality of spines can extend along a longitudinal axis and can be configured to expand away from the longitudinal axis to form a basket shape. The first loop member can include a first pair of spines of the plurality of spines and a distal spine hub disposed approximate a distal end of the end effector. The distal spine hub can include a plurality of openings therethrough. The second loop member can include a second pair of spines of the plurality of spines and a distal segment extending through at least one opening of the plurality of openings. The one or more electrodes can be coupled to each spine of the plurality of spines.

Another exemplary end effector of a medical probe can include a plurality of spines, a structural support member, a spiral inductor, and one or more electrodes. The plurality of spines can extend along a longitudinal axis and can be configured to expand away from the longitudinal axis to form a basket shape. The structural support member can extend through a spine of the plurality of spines. The spiral inductor can be disposed approximate a distal end of the end effector. The spiral inductor can have a central axis along the longitudinal axis. The spiral inductor can be electrically coupled to the structural support member so that the structural support member is configured to transmit electrical signals from the spiral inductor along the spine. The one or more electrodes can be coupled to each spine of the plurality of spines.

Another exemplary end effector of a medical probe can include a support frame, an atraumatic structure, and one or more electrodes. The support frame can be movable between a delivery configuration and a basket configuration. The support frame can include a plurality of spines configured to self-expand away from a longitudinal axis from a proximal portion to a distal spine portion to form a basket shape in the basket configuration. The distal spine portion can define a cloverleaf structure disposed around the longitudinal axis. The cloverleaf structure can define a central cutout with a central area disposed about the longitudinal axis. The cloverleaf structure can be aligned cylindrically about the longitudinal axis in the delivery configuration and angled radially from the longitudinal axis in the basket configuration. The atraumatic structure can cover a portion of the cloverleaf structure of the support frame. The atraumatic structure can include a plurality of radial extensions each extending along a respective spine of the plurality of spines such that the radial extensions are configured to slide along the respective spine as the support frame moves between the delivery configuration and the basket configuration. The one or more electrodes can be coupled to each spine of the plurality of spines.

BRIEF DESCRIPTION OF THE DRAWINGS

While the specification concludes with claims, which particularly point out and distinctly claim the subject matter described herein, it is believed the subject matter will be better understood from the following description of certain examples taken in conjunction with the accompanying drawings, in which like reference numerals identify the same elements. The figures depict one or more implementations of the inventive devices, by way of example only, not by way of limitation.

FIGS. 6A and 6B are illustrations of a cross-section of an inflatable member coupled to a spine as indicated in FIG. 2 according to aspects of the present invention, wherein FIG. 6A illustrates the inflatable member in a deflated state and FIG. 6B illustrates the inflatable member in an inflated state.

DETAILED DESCRIPTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives, and uses of the invention, including what is presently believed to be the best mode of carrying out the invention.

As used herein, the terms “about” or “approximately” for any numerical values or ranges indicate a suitable dimensional tolerance that allows the part or collection of components to function for its intended purpose as described herein. More specifically, “about” or “approximately” may refer to the range of values ±10% of the recited value, e.g., “about 90%” may refer to the range of values from 81% to 99%.

In addition, as used herein, the terms “patient,” “host,” “user,” and “subject” refer to any human or animal subject and are not intended to limit the systems or methods to human use, although use of the subject invention in a human patient represents a preferred embodiment. As well, the term “proximal” indicates a location closer to the operator whereas “distal” indicates a location further away to the operator or physician.

When used herein, the terms “tubular” and “tube” are to be construed broadly and are not limited to a structure that is a right cylinder or strictly circumferential in cross-section or of a uniform cross-section throughout its length. For example, the tubular structure or system is generally illustrated as a substantially right cylindrical structure. However, the tubular system may have a tapered or curved outer surface without departing from the scope of the present invention.

As used herein, the term “proximal” indicates a location closer to the operator or physician whereas “distal” indicates a location further away to the operator or physician.

Alternative apparatus and system features and alternative method steps are presented in example embodiments herein. Each given example embodiment presented herein can be modified to include a feature and/or method step presented with a different example embodiment herein where such feature and/or step is compatible with the given example as understood by a person skilled in the pertinent art as well as where explicitly stated herein. Such modifications and variations are intended to be included within the scope of the claims.

Figure 1:
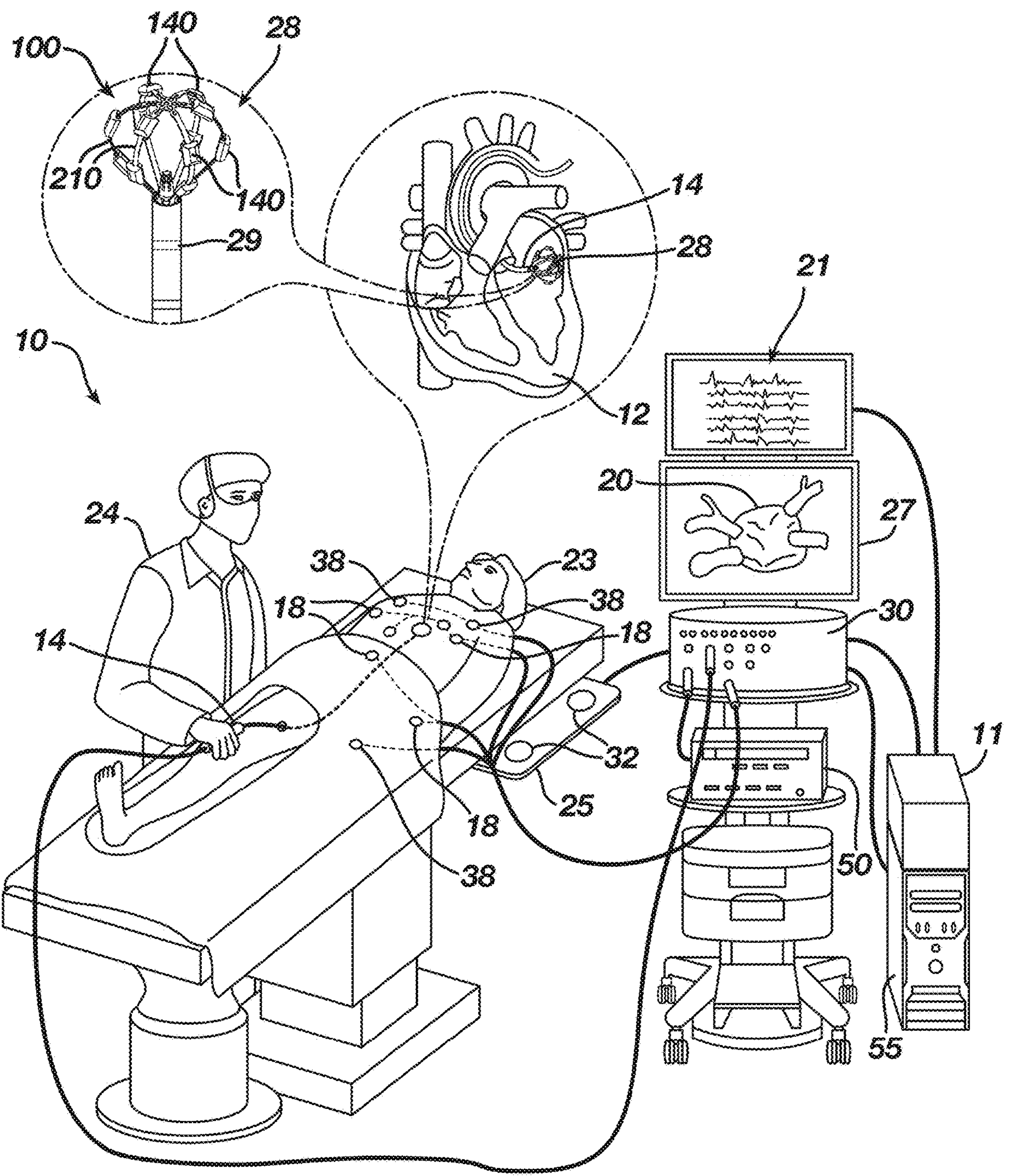
FIG. 1 is an illustration of an example catheter-based electrophysiology mapping and ablation system according to aspects of the present invention.

FIG. 1 is an illustration showing an example catheter-based electrophysiology mapping and ablation system 10. The system 10 includes multiple catheters, which are percutaneously inserted by a physician 24 through the patient's vascular system into a chamber or vascular structure of a heart 12. Typically, a delivery sheath catheter is inserted into the left or right atrium near a desired location in the heart 12. Thereafter, a plurality of catheters can be inserted into the delivery sheath catheter so as to arrive at the desired location. The plurality of catheters may include catheters dedicated for sensing Intracardiac Electrogram (IEGM) signals, catheters dedicated for ablating and/or catheters dedicated for both sensing and ablating. An example catheter 14 is illustrated herein. The physician 24 brings a distal tip 28 of the catheter 14 into contact with the heart wall for sensing a target site in the heart 12 and/or ablation.

The illustrated catheter 14 is an exemplary catheter that includes one, and preferably multiple, electrodes 140 optionally distributed over a plurality of spines 110 at distal tip 28 and configured to sense the IEGM signals. Catheter 14 may additionally include a position sensor 29 embedded in or near distal tip 28 for tracking position and orientation of distal tip 28. Optionally and preferably, position sensor 29 is a magnetic based position sensor including three magnetic coils for sensing three-dimensional (3D) position and orientation.

A magnetic based position sensor 29 may be operated together with a location pad 25 including a plurality of magnetic coils 32 configured to generate magnetic fields in a predefined working volume. Real time position of a distal tip 28 of the catheter 14 may be tracked based on magnetic fields generated with a location pad 25 and sensed by a magnetic based position sensor 29. Details of the magnetic based position sensing technology are described in U.S. Pat. Nos. 5,391,199; 5,443,489; 5,558,091; 6,172,499; 6,239,724; 6,332,089; 6,484,118; 6,618,612; 6,690,963; 6,788,967; 6,892,091 incorporated by reference herein.

The system 10 includes one or more electrode patches 38 positioned for skin contact on the patient 23 to establish location reference for location pad 25 as well as impedance-based tracking of electrodes 140. For impedance-based tracking, electrical current is directed toward electrodes 140 and sensed at electrode skin patches 38 so that the location of each electrode can be triangulated via the electrode patches 38. Details of the impedance-based location tracking technology are described in U.S. Pat. Nos. 7,536,218; 7,756,576; 7,848,787; 7,869,865; and 8,456,182 incorporated by reference herein.

The magnetic based position sensor 29 can be used to calibrate impedance-based tracking of the electrodes 40. The workstation 55 can be configured to locate the distal tip 28 of the catheter 14 based on the magnetic sensor 29 and a plurality of reference electromagnetic (EM) sensors. The reference EM sensors can be configured to define an EM coordinate system and a body coordinate system.

A recorder 11 displays electrograms 21 captured with body surface ECG electrodes 18 and intracardiac electrograms (IEGM) captured with electrodes 140 of the catheter 14. The recorder 11 may include pacing capability for pacing the heart rhythm and/or may be electrically connected to a standalone pacer.

The system 10 can include an ablation energy generator 50 that is adapted to conduct ablative energy to one or more of electrodes at a distal tip of a catheter configured for ablating. Energy produced by the ablation energy generator 50 may include, but is not limited to, radiofrequency (RF) energy or pulsed-field ablation (PFA) energy, including monopolar or bipolar high-voltage DC pulses as may be used to effect irreversible electroporation (IRE), or combinations thereof.

A patient interface unit (PIU) 30 is an interface configured to establish electrical communication between catheters, electrophysiological equipment, power supply and a workstation 55 for controlling operation of system 10. Electrophysiological equipment of the system 10 may include for example, multiple catheters, a location pad 25, body surface ECG electrodes 18, electrode patches 38, an ablation energy generator 50, and a recorder 11. Optionally and preferably, the PIU 30 includes processing capability for implementing real-time computations of location of the catheters and for performing ECG calculations.

The workstation 55 includes memory, processor unit with memory or storage with appropriate operating software loaded therein, and user interface capability. The workstation 55 can be configured to provide multiple functions, optionally including (1) modeling the endocardial anatomy in three-dimensions (3D) and rendering the model or an anatomical map 20 for display on a display device 27; (2) displaying on the display device 27 activation sequences (or other data) compiled from recorded electrograms 21 in representative visual indicia or imagery superimposed on the rendered anatomical map 20; (3) displaying real-time location and orientation of multiple catheters within the heart chamber; and (4) displaying on the display device 27 sites of interest such as places where ablation energy has been applied. One commercial product embodying elements of the system 10 is available as the CARTO™ 3 System, available from Biosense Webster, Inc., 31A Technology Drive, Irvine, CA 92618.

Figure 2:
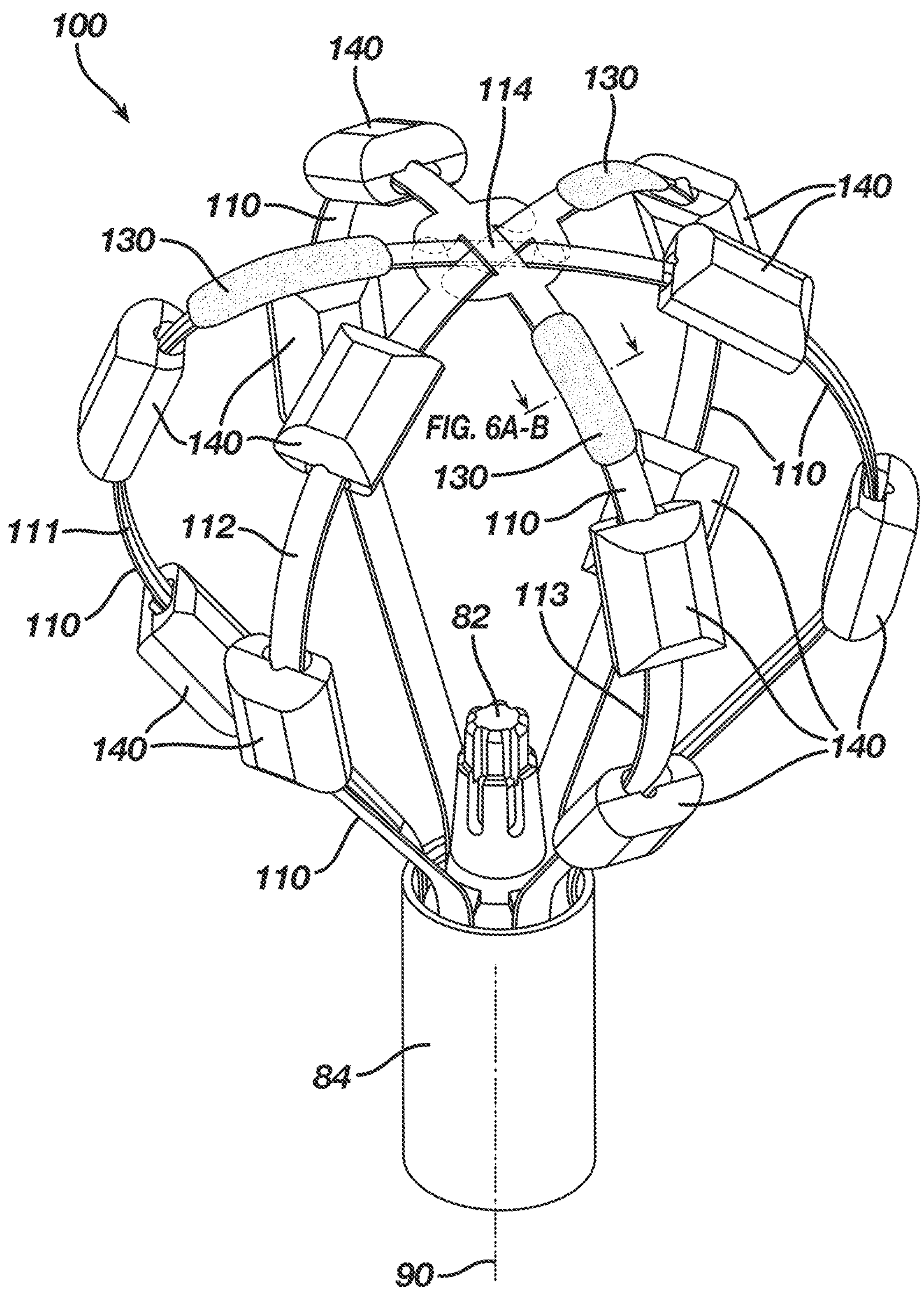
FIG. 2 is an illustration of aspects of a distal portion of a basket catheter usable with the system illustrated in FIG. 1 according to aspects of the present invention.

FIG. 2 is an illustration of aspects of a distal portion of a basket catheter usable with the system illustrated in FIG. 1. The catheter 14 illustrated in FIG. 1 can be modified to include features of an end effector 100 of the basket catheter illustrated in FIG. 2. The basket catheter includes a shaft 84 defining a longitudinal axis 90. The end effector 100 includes spines 110 that extend along the longitudinal axis 90 and are configured to expand away from the longitudinal axis to form a basket shape as illustrated in FIG. 2. The spines 110 are further configured to collapse toward the longitudinal axis so that the end effector 100 can be retracted through a delivery sheath of the system 10 illustrated in FIG. 1. During a medical procedure, medical professional 24 can deploy the end effector 100 by extending the shaft 84 distally through a guide sheath (not illustrated) so that it exits the distal end of the guide sheath and expands to the basket shape. The end effector 100 can be collapsed again when the end effector is retracted proximally into the distal end of the sheath.

The spines 110 may have an elliptical (e.g., circular), rectangular shape, and/or flat cross-sectional shape. The spines 110 can include a support structure, strut, and/or frame that includes a flexible, resilient material e.g., a shape-memory alloy such as nickel-titanium, also known as Nitinol. The end effector 100 includes electrodes 140 that are coupled to the spines 110. The electrodes 140 can have a lumen through which proximal ends of the spines 110 are inserted during assembly of the catheter. The electrodes 140 can otherwise be coupled to the spines 110 by a suitable means as understood by a person skilled in the pertinent art. The catheter 14 can include a hub 82 that can be configured to retain proximal ends of the spines 110 in the shaft 84. The hub 82 can further be configured to provide an irrigation flow to the end effector 100.

The end effector 100 can include loop members 111, 112, 113 that each include a pair of spines 110 and a central region overlapping at a central spine intersection 114 approximate a distal end of the end effector 100. The loop members 111, 112, 113 can be formed by cutting a planar sheet of flexible resilient material or by cutting a tubular material. Forming the loop members 111, 112, 113 from a planar sheet is preferred over a tubular material due to comparatively lower cost and ease of manufacturing of the planar sheet.

The electrodes 140 positioned on the spines 110 can be configured to deliver ablation energy (RF and/or IRE) to tissue in the heart 12. Additionally, or alternatively, the electrodes 140 can also be used to determine the location of basket assembly 100 and/or to measure a physiological property such as local surface electrical potentials at respective locations on tissue in heart 12. The electrodes 140 can be biased such that a greater portion of the one or more electrodes 140 face outwardly from basket assembly 100 such that the one or more electrodes 140 deliver a greater amount of electrical energy outwardly away from the basket assembly 100 (i.e., toward the heart 12 tissue) than inwardly.

Examples of materials ideally suited for forming electrodes 140 include gold, platinum, and palladium (and their respective alloys). These materials also have high thermal conductivity which allows the minimal heat generated on the tissue (i.e., by the ablation energy delivered to the tissue) to be conducted through the electrodes to the back side of the electrodes (i.e., the portions of the electrodes on the inner sides of the spines), and then to the blood pool in heart 12.

Figure 6A:
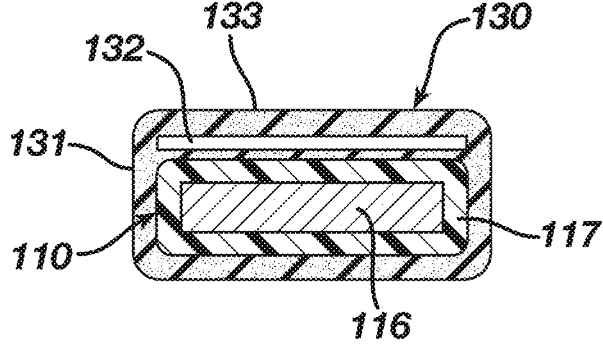
Figure 6B:
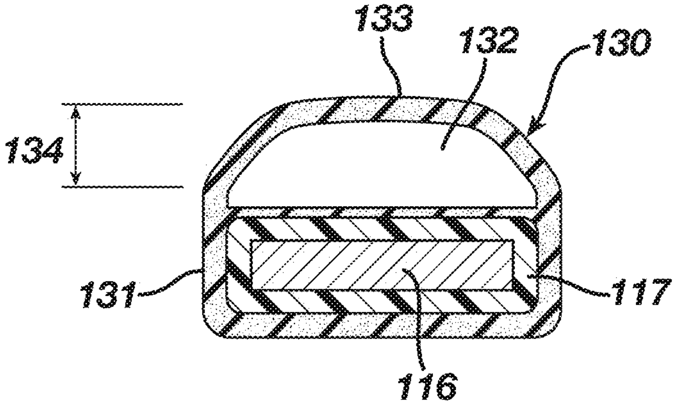

The basket assembly 100 further includes inflatable members 130 discussed in greater detail in relation to FIGS. 6A and 6B.

The basket assembly 100 can further include an atraumatic structure 420 (FIGS. 10 and 11) covering the central regions of the loop members 111, 112, 113 to provide an atraumatic surface to shield the central regions of the loop members 111, 112, 113 from contacting tissue.

Figure 3:
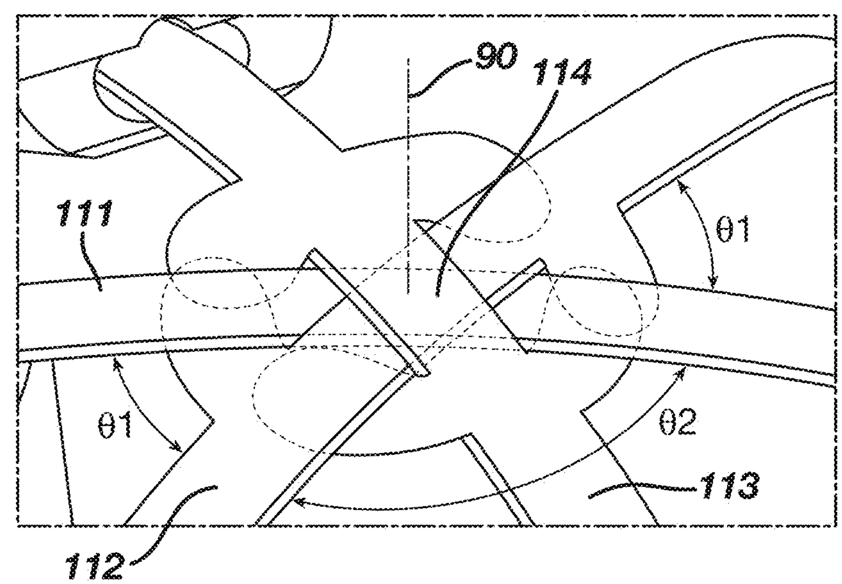
FIG. 3 is a magnified view of a distal end of an end effector of the basket catheter as indicated in FIG. 2 according to aspects of the present invention.

FIG. 3 is a magnified view of a distal end of an end effector of the basket catheter as indicated in FIG. 2. A first loop member 111, a second loop member 112, and a third loop member 113 each respectively have a central portion across the central spine intersection 114. Alternative, the end effector 100 can include two, four, five, or six loop members. As illustrated, the three loop members are positioned at an angle to each other such that there is an acute angle θ1 and an obtuse angle θ2 between any set of two loop members. A third loop member bisects the obtuse angle θ2. Preferably the acute angle θ1 measures about 60° and the obtuse angle θ2 measures about 120° so that the spines 110 are spaced equally around a circumference of the basket assembly. Likewise, an end effector 100 having two, four, five, or six loop members preferably has spines that are spaced equally around a circumference of the basket assembly.

Figure 4:
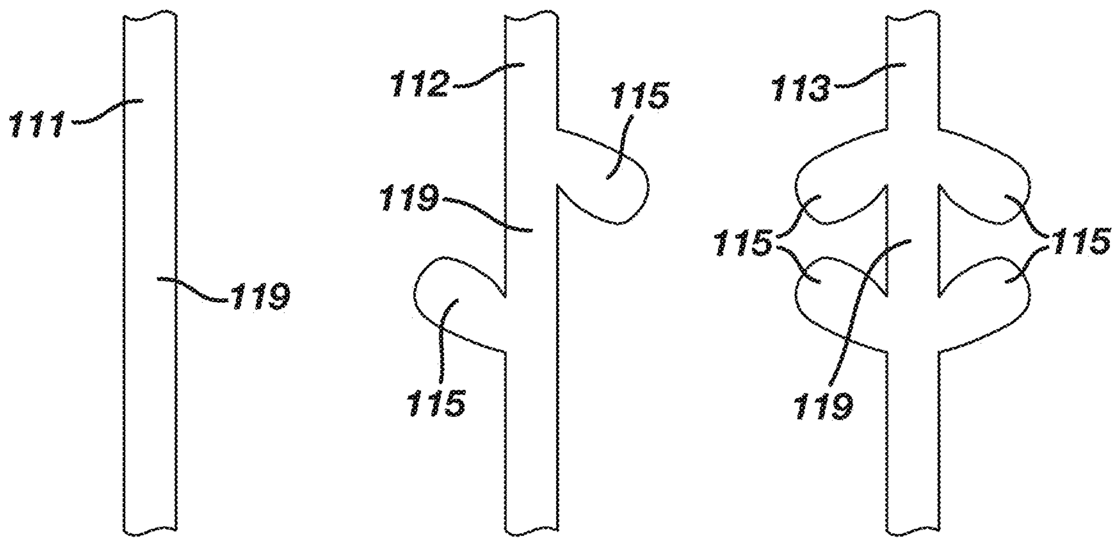
FIG. 4 is an illustration of disassembled spine segments from the distal end of the end effector illustrated in FIG. 3 according to aspects of the present invention.

FIG. 4 is an illustration of central regions of disassembled loop member segments from the distal end of the end effector 100 illustrated in FIG. 3. The central region of the first loop member 111 has a substantially uniform width and does not include extensions. The central region of the second loop member 112 includes two extensions 115. The central region of the third loop member 113 includes four extensions 115. Each loop member 111, 112, 113 has a respective middle portion 119 that crosses the longitudinal axis 90.

Referring collectively to FIGS. 2 through 4, as illustrated, the central regions of the loop members 111, 112, 113 are stacked at the central spine intersection 114 in an inner-to-outer order such that the loop members are ordered: first loop member 111, second loop member 112, and third loop member 113 in the inner-to-outer order. Central regions of the second loop member 112 and third loop member 113 include extensions 115 that are configured to overlap the first loop member 111 out of order from the inner-to-outer order. For instance, where the extensions 115 of the second loop member 112 and third loop member 113 overlap the first loop member 111, the order of loop members is: third loop member 113, second loop member 112, and first loop member 111. The central portion of the first loop member 111 is distal of extensions 115 of both the second loop member 112 and the third loop member 113. Extensions 115 of the third loop member 113 also overlap the second loop member 112 out of order from the inner-to-outer order.

The middle portion 119 of the first loop member 111 is proximal of both middle portions 119 of the second and third loop members 112, 113. The middle portion 119 of the second loop member 112 is disposed over a distal surface of the middle portion 119 of the first loop member 111. Extensions 115 of the second loop member 112 is disposed under a proximal surface of the first loop member 111. The extensions 115 from the second loop member 112 extend through the acute angle θ1 between the first loop member 111 and the second loop member 112 on either side of central spine intersection 114. The middle portion 119 of the third loop member 113 is disposed over a distal surface of the middle portion 119 of the second loop member 112. The central region of the third loop member includes extensions 115 that extend under a proximal surface of the central region of the second loop member 112 and extensions 115 that extend under a proximal surface of the central region of the first loop member 111.

The central regions of the loop members 111, 112, 113 are overlapped to couple the loop members 111, 112, 113 together at the distal end of the end effector. The central regions of the loop members 111, 112, 113 are configured to interlock to maintain connection between the loop members approximate the distal end of the end effector 100. Preferably, the loop members 111, 112, 113 are configured to maintain consistent angles θ1, θ2 between the spines 110 during use of the catheter 14. The loop members 111, 112, 113 fit together similar to cardboard box flaps that are folded over and under each other to close the box.

Figure 5A:
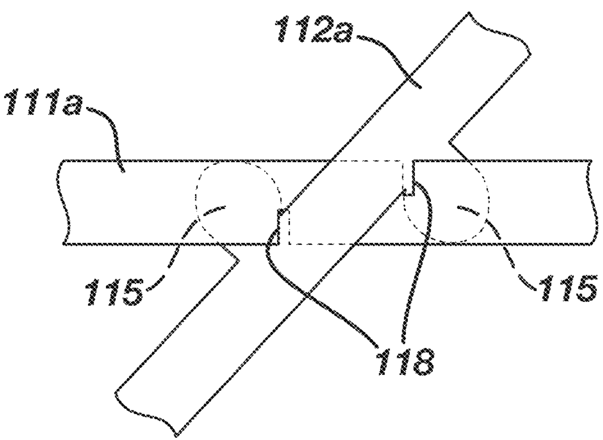
FIG. 5A is an illustration of two interlocked spine segments having at least one spine segment modified to include a notch into which the other spine segment can be received according to aspects of the present invention.

FIG. 5A is an illustration of two interlocked central regions of another example first loop member 111*a* and second loop member 112*a*. The central region of the first loop member 111*a* is modified to include a notch 118 into which the central region of the second loop member 112*a* is received. One or more of the loop members 111, 112, 113 illustrated in FIGS. 2 through 4 can be modified to include a notch 118 as illustrated in FIG. 5A.

Figure 5B:
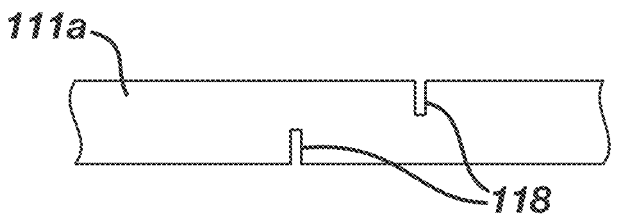
FIGS. 5B and 5C are illustrations of the two spine segments of FIG. 5A disassembled from each other according to aspects of the present invention.
Figure 5C:
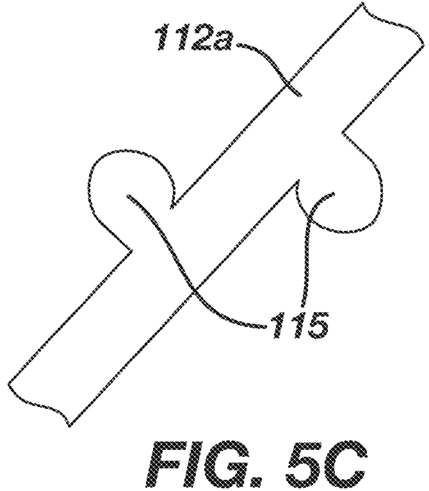

FIGS. 5B and 5C are illustration of central regions of the two loop members 111*a*, 1112*a* of FIG. 5A disassembled from each other. The first loop member 111*a* includes notches 118 into which the second loop member 112*a* is received. Additionally, or alternatively, the second loop member 112*a* can include similar notches 118 into which the first loop member 111*a* and/or the third loop member can be received. Preferably, the notches 118 are positioned to receive a central region of a loop member to engage with an extension 115 to inhibit movement of the central regions of the loop members in relation to each other.

FIGS. 6A and 6B are illustrations of a cross-section of an inflatable member 130 coupled to a spine as indicated in FIG. 2. FIG. 6A illustrates the inflatable member 130 in a deflated state and FIG. 6B illustrates the inflatable member in an inflated state. Referring collectively to FIGS. 2, when the inflatable members 130 are inflated, the central spine intersection 114 can be prevented from pressing into tissue with a force that causes tissue damage. The inflatable members 130 can be deflated so that the end effector 100 is sized to translate through a guide sheath. When the end effector 100 exits the guide sheath and expands, the inflatable members 130 can be inflated to inhibit the distal end of the basket assembly (i.e., approximate the central spine intersection 114) from impinging on tissue and/or prevent the distal end of the basket assembly from contacting tissue.

As illustrated in FIG. 2, the end effector 100 can include three inflatable members 130 spaced equally around the central spine intersection 114 and equally around the longitudinal axis 90. The end effector 100 may alternatively include one, two, four, five, or six inflatable members 130. The illustrated end effector 100 has six spines 110. Electrodes 140 are positioned more distally on half of the spines 110 and more proximately on half of the spines 110 in an alternating fashion so that electrodes 140 nest next to each other when the basket assembly is collapsed. The spines 110 having more proximally spaced electrodes 140 include the inflatable members 130 positioned distal of the electrodes 140. A similar configuration can be achieved with a basket catheter having eight or ten spines, wherein electrodes 140 are positioned more distally on half of the spines 110 and more proximately on half of the spines 110 in an alternating fashion so that electrodes 140 nest next to each other when the basket assembly is collapsed and inflatable members 130 are positioned on spines with proximally positioned electrodes 140. A basket catheter with eight spines may therefore have four inflatable members 130, and a basket catheter with ten spines may therefore have five inflatable members 130.

As illustrated in FIGS. 6A and 6B, the spine 110 can include a frame strut 116 extending through a jacket 117. The jacket 117 can electrically insulate the frame of the basket assembly from the electrodes 140. The inflatable member 130 is coupled to the strut 110. The inflatable member includes a resilient membrane 131 with an inflatable chamber 132 that can be inflated and deflated to cause a distal surface 133 of the inflatable member 130 to move a distance 134. Inflation can be by irrigation fluid (not illustrated) or other media entering the chamber 132, and then the inflation media can be removed to deflate the chamber 132.

Figures 7, 8A:
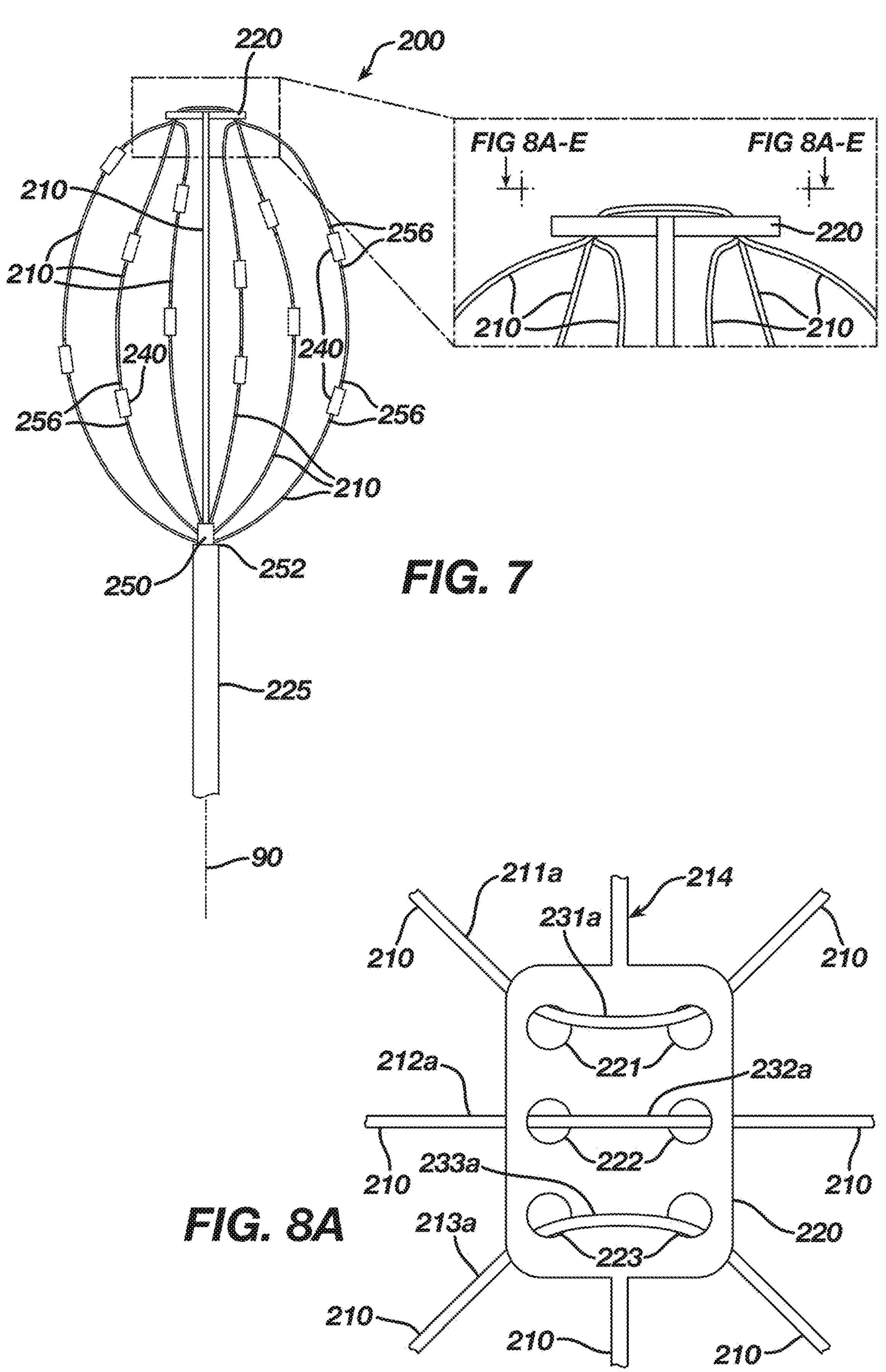
FIG. 7 is an illustration of the basket catheter modified to include a spine hub according to aspects of the present invention.
FIGS. 8A, 8B, 8C, 8D, and 8E illustrate variations of the spine hub at the distal end of the end effector of the basket catheter according to aspects of the present invention.

FIG. 7 is an illustration of a second exemplary basket assembly 200. The catheter 14 illustrated in FIG. 1 can be modified to include features of the second exemplary basket assembly 200. Further, compatible features of the second exemplary basket assembly 200 can be combined with features of the basket assembly illustrated in FIGS. 1 through 6A and 6B. The end effector 200 includes loop members, each with a pair of spines 210. The spines 210 extend along the longitudinal axis 90. As illustrated, the spines 210 are expanded away from the longitudinal axis 90 to form a basket shape in a deployed configuration. The spines 210 can collapse toward the longitudinal axis 90 in a collapsed configuration. A proximal end 250 of the end effector 200 is connected to a distal end 252 of a shaft 225 of the catheter.

The end effector 200 includes a spine hub 220 disposed approximate a distal end of the end effector 200. The end effector 200 includes loop members having spines 210 and electrodes 240 coupled to the spines. The electrodes 240 can be coupled to the spines 210 as disclosed elsewhere herein. The end effector 200 can further include irrigation outlets 256. The end effector 200 can include a puller 246 that can be manipulated to move the end effector between a collapsed configuration and a deployed configuration. The end effector 200 can further include compatible features disclosed in U.S. Patent Publication No. 2022/0361942, incorporated herein by reference and attached in the Appendix of parent priority application No. 63/505,978.

Figure 8B:
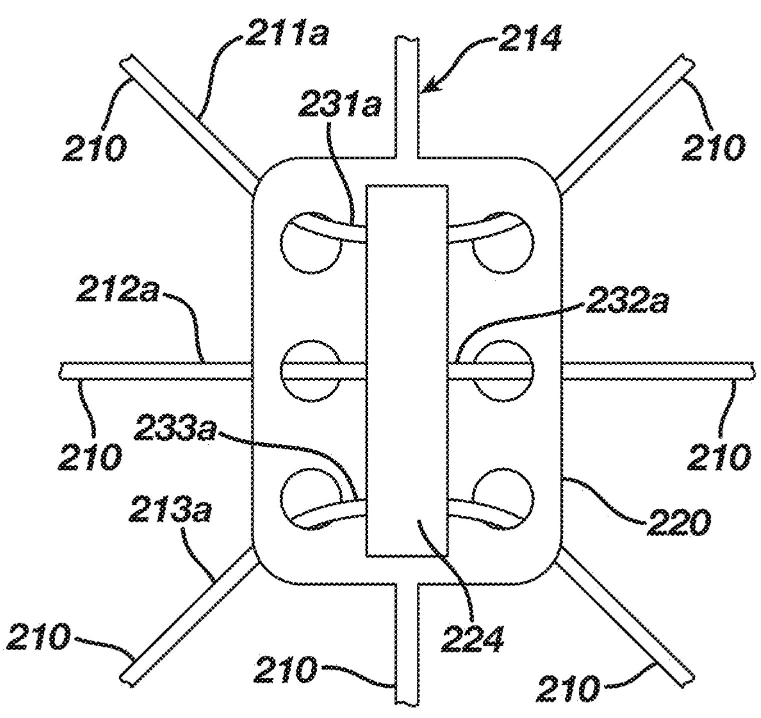
Figure 8C:
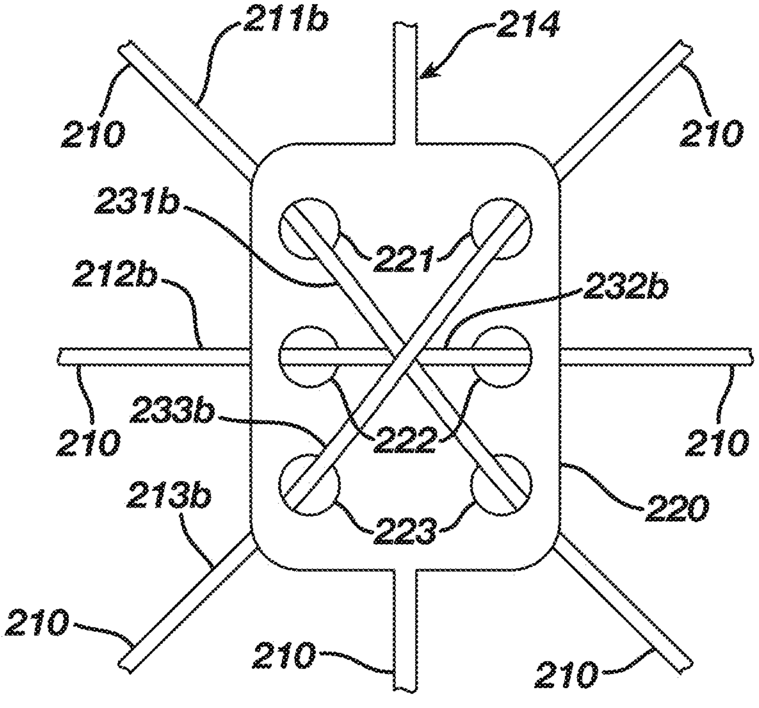
Figure 8D:
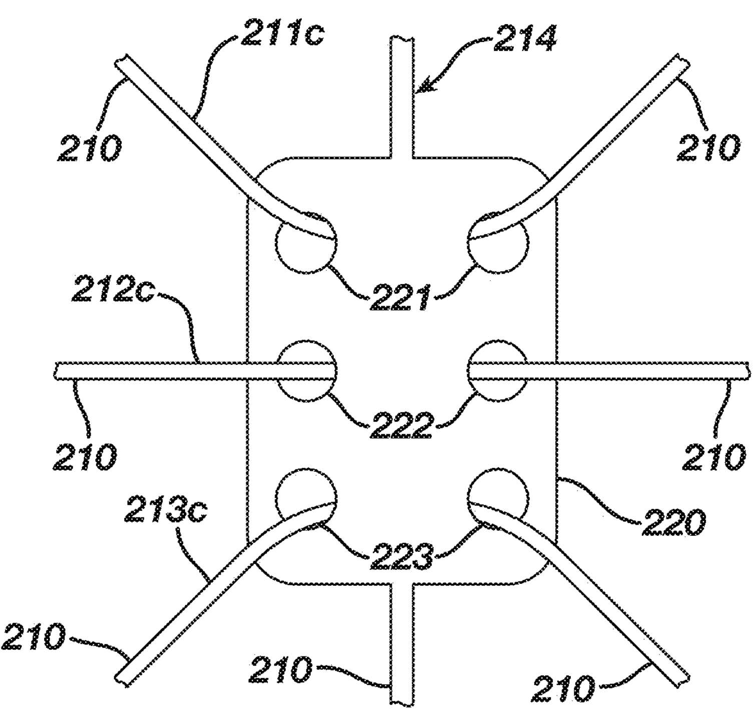
Figure 8E:
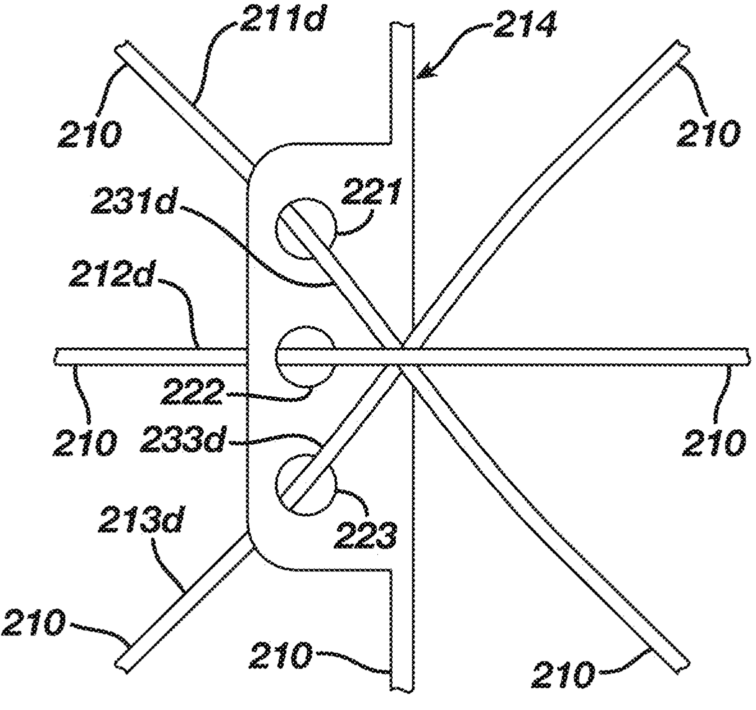

FIGS. 8A, 8B, 8C, 8D, and 8E illustrate variations of the spine hub 220 at the distal end of the end effector of the basket catheter as indicated in FIG. 7. FIGS. 8A through 8D depict a spine hub 220 with six openings 221, 222, 223 and a support spine loop 214. FIG. 8E depicts a spine hub 220 with three openings 221, 222, 223 and a support spine loop 214. Each of the spine hubs 220 is couple three additional spine loops approximate the distal end of the end effector 200.

The spine hub 220, including the support spine loop 214 can be cut from a single planar sheet. The end effector 200 can be otherwise configured so that one of the loop members of the end effector includes the spine hub 220.

As illustrated, the end effector 200 includes eight spines and four spine loops: one spine loop including the support spine loop 214 and the spine hub 220; and three additional spine loops that extend through openings of the spine hub 220. Alternatively, the spine hub 220 need not include the support spine loop 214. The spine hub 220 can also be configured with more or fewer holes to coupled more or fewer spine loops.

FIG. 8A depicts a first spine loop 211*a* that extends through a first pair of openings 221 and has a first distal portion 231*a* across a distal surface of the spine hub 220; a second spine loop 212*a* that extends through a second pair of openings 222 and has a second distal portion 232*a* across a distal surface of the spine hub 220; and a third spine loop 213*a* that extends through a third pair of openings 223 and has a third distal portion 233*a* across a distal surface of the spine hub 220. The distal portions 231*a*, 232*a*, 233*a* are approximately parallel to each other.

FIG. 8B depicts the spine hub 220 and spine loops 211*a*, 212*a*, 213*a* configured similar to FIG. 8A. The end effector 200 further includes an atraumatic cover 224 over the distal portions 231*a*, 232*a*, 233*a* of the spine loops 211*a*, 212*a*, 213*a* to provide an atraumatic surface at the distal end of the end effector 200.

FIG. 8C depicts spine loops 211*b*, 212*b*, 213*b* having distal portions 231*b*, 232*b*, 233*b* that cross over a distal surface of the spine hub 220 so that the distal portions 231*b*, 232*b*, 233*b* cross-over each other to overlap at a central intersection.

FIG. 8D depicts a first spine loop 211*c* that extends through a first pair of openings 221 and has a first distal portion (not illustrated) across a proximal surface of the spine hub 220; a second spine loop 212*c* that extends through a second pair of openings 222 and has a second distal portion (not illustrated) across a proximal surface of the spine hub 220; and a third spine loop 213*c* that extends through a third pair of openings 223 and has a third distal portion (not illustrated) across a proximal surface of the spine hub 220. The distal portions are approximately parallel to each other. Likewise, the distal portions 231*b*, 232*b*, 233*b* can cross-over each other across a proximal surface of the spine hub 220.

FIG. 8E depicts a spine hub 220 in which the spine loops 211*d*, 212*d*, 213*d* each respectively extend through only one opening 221, 222, 223. Distal portions 231*d*, 232*d*, 233*d* of the spine loops 211*d*, 212*d*, 213*d* cross over each other across a distal surface of the spine hub 220. Alternatively, the distal portions 231*d*, 232*d*, 233*d* can cross a proximal surface of the spine hub 220. Alternatively, the distal portions 231*d*, 232*d*, 233*d* can be substantially parallel to each other.

The end effector 200 can be modified to include one or more inflatable members 130 (FIGS. 2, 6A, and 6B) coupled to one or more spines 210 approximate a distal end of the end effector 200. The inflatable members 130 can be inflated in a deployed configuration to inhibit the spine hub 220 and/or distal segments of the loop members from impinging on tissue. The inflatable members 130 can be inflated in a deployed configuration to prevent the spine hub 220 and/or distal segments of the loop members from contacting tissue. The inflatable members 130 can be deflated to collapse for delivery through a sheath.

Figure 9:
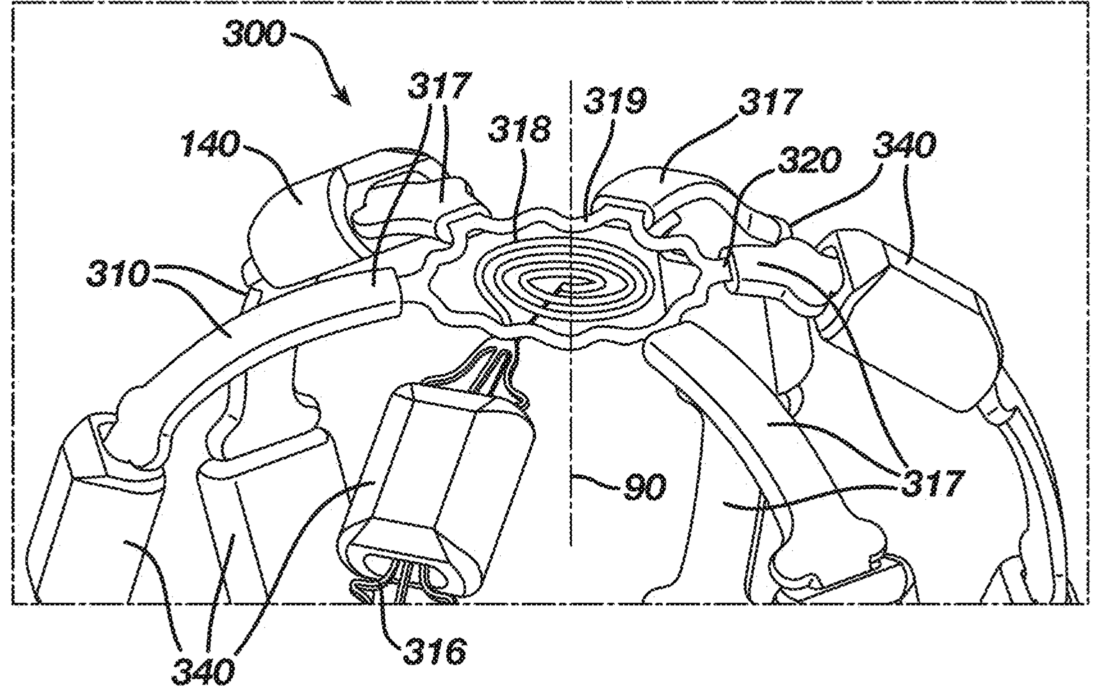
FIG. 9 is an illustration of the basket catheter modified to include a spiral sensor electrically connected to a support structure of a spine of the basket assembly according to aspects of the present invention.

FIG. 9 is an illustration of a distal portion of a third exemplary end effector 300. The basket catheter 14 can be modified to include a spiral sensor 318 (spiral inductor, inductive sensor) electrically connected to a support structure 316 of a spine 310 of the basket assembly. The end effector 300 includes spines 310 that extend along the longitudinal axis and are configured to collapse toward the longitudinal axis 90 in a collapsed configuration and expand away from the longitudinal axis 90 to form a basket shape in a deployed configuration. The end effector can include one or more support members 316, 320 extending through the spines 310 and providing structural support to the basket assembly 300 to facilitate expansion of the basket assembly 300 to the deployed configuration. The support members 316, 320 may be formed of a flexible, resilient material e.g., a shape-memory alloy such as nickel-titanium, also known as Nitinol. The end effector 300 can include a spiral inductor 318 disposed approximate a distal end of the end effector 300. The spiral inductor 318 is wound about a central axis along the longitudinal axis 90. The spiral inductor 318 is electrically coupled to a structural support member 316 extending through one of the spines 310. As illustrated, the structural support member 316 is separate from the structural support member 320 extending through the remaining spines 310. The structural support member 316 that is electrically coupled to the spiral inductor 318 is configured to transmit electrical signals from the spiral inductor 318 along the respective spine 310 to the workstation 55 (FIG. 1). Alternatively, multiple support members, or the entire frame of the basket assembly may be electrically coupled to the spiral inductor 318. The spiral inductor 318 and support member 316 can be formed from a common sheet or tube of material and may include a flexible, resilient material e.g., a shape-memory alloy such as nickel-titanium, also known as Nitinol.

The end effector 300 further includes electrodes 340 coupled to the spines 310. The electrodes 340 can be configured similarly to electrodes 140, 240 disclosed elsewhere herein. The electrodes 340 can be coupled to the spines 310 as disclosed elsewhere herein. The spines 310 can include an insulative jacket 317 over the support members 316, 320 to electrically insulate the support member(s) 316 from the electrodes 140. The spiral inductor 318 may be electrically isolated from the electrodes 140 by insulative jacket(s) 317. The insulative jacket is omitted in FIG. 9 on the support member 316 that is electrically coupled to the spiral inductor 318 for the sake of illustration. The support member 316 can otherwise be referred to as a strut. The illustrated end effector 300 further includes a sinusoidal member 319 connecting to distal ends of struts extending through the remaining spines 310 of the end effector 300. The sinusoidal member 319 may be covered by the jackets 317 or other insulating cover.

The end effector 300 can be modified to include one or more inflatable members 130 (FIGS. 2, 6A, and 6B) coupled to one or more spines 310 approximate the distal end of the end effector 300 such that the inflatable member(s) 130 is/are configured to collapse for delivery through a sheath and is/are configured to inflate in a deployed configuration, and such that the inflatable member(s) in the deployed configuration prevent the distal end of the basket assembly 300 from contacting tissue.

Figure 10:
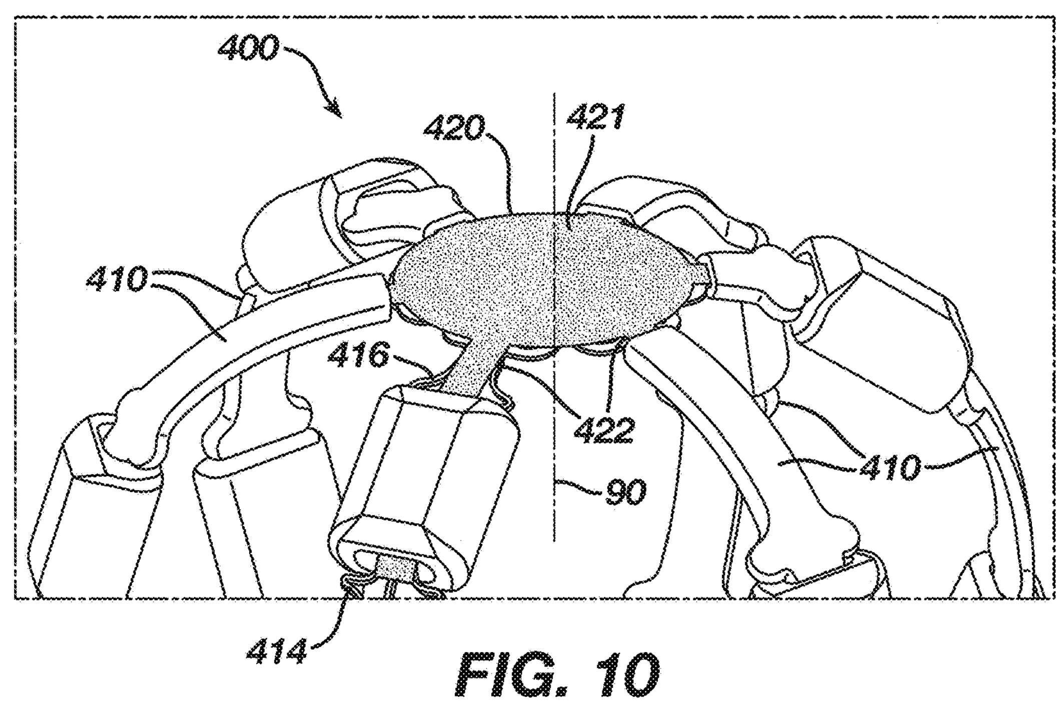
FIG. 10 is an illustration of the basket catheter modified to include a distal atraumatic cover at the distal end of the end effector of the basket catheter according to aspects of the present invention.

FIG. 10 is an illustration of the basket catheter 14 illustrated in FIG. 1 modified to include another exemplary end effector 400 having a distal atraumatic structure 420 at the distal end of the end effector 400. The end effector 400 includes spines 410 and electrodes 440 that can be configured similarly to spines 110, 210, 310 and electrodes 140, 240, 340 disclosed elsewhere herein. The electrodes 440 are coupled to the spines 410 as disclosed elsewhere herein. The spines 410 include a support frame 414 that may include a flexible, resilient material e.g., a shape-memory alloy such as nickel-titanium, also known as Nitinol. The support frame 414 is movable between a delivery configuration and a basket configuration and includes struts 416 that extend through the spines 410 so that the spines 410 are configured to self-expand away from the longitudinal axis 90 from a proximal portion to a distal spine portion to form a basket shape in the basket configuration.

The atraumatic structure 420 includes a circular central portion 421 and radial extensions 422 each extending along a respective spine 410. The circular central portion 421 is configured to provide an atraumatic surface configured to shield the underlying distal portion of the support frame 414 from contacting tissue. The radial extensions 422 are configured to slide along the respective spine 410 as the support frame 414 moves between the delivery configuration and the basket configuration.

Figure 11:
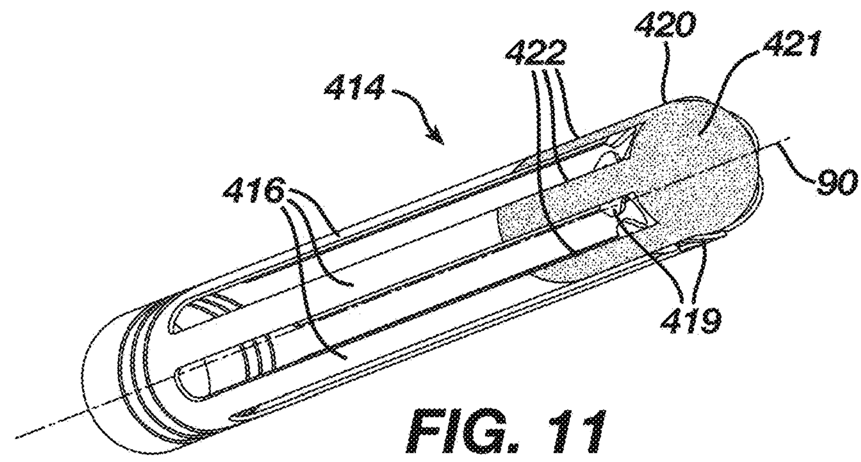
FIG. 11 is an illustration of a frame of the modified catheter of FIG. 10 in a tubular configuration according to aspects of the present invention.

FIG. 11 is an illustration of the support frame 414 of the end effector 400 of FIG. 10 in a tubular configuration and including the atraumatic structure 420. The proximal ends of struts 416 can be joined as illustrated, or the proximal ends of struts 416 can be free so that electrodes 430 can be slid onto spine proximal ends during assembly. The atraumatic structure 420 is positioned at a distal end of the support frame 414. The radial extensions 422 are translated distally along the struts 416 and spines 410 as the support frame 414 moves from the deployed configuration illustrated in FIG. 10 to the collapsed configuration illustrated in FIG. 11. The end effector 400 may include a spring coupler that couples the radial extensions 422 to the spines 410 in a spring-loaded fashion to facilitate translation of the radial extensions 422 along the spines 410 as the end effector 400 moves between the deployed and collapsed configurations.

Figure 12:
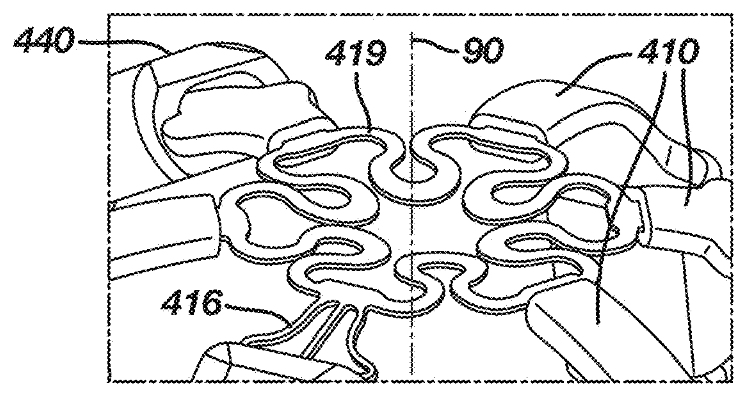
FIG. 12 is an illustration of the distal end of the end effector of the modified catheter of FIG. 10 with the distal atraumatic cover removed for the sake of illustration according to aspects of the present invention.

FIG. 12 is an illustration of the distal end of the end effector 400 of FIG. 10 with the distal atraumatic cover removed for the sake of illustration. The distal portion of the support frame 414 defining a cloverleaf structure 419 disposed around the longitudinal axis 90. The cloverleaf structure 419 defines a central cutout with a central area disposed about the longitudinal axis 90. The cloverleaf structure 419 is aligned cylindrically about the longitudinal axis 90 in the delivery configuration and angled radially from the longitudinal axis 90 in the basket configuration. The circular central portion 421 of the atraumatic structure 420 covers a portion of the cloverleaf structure 419. The support frame 414 can be modified to include the spiral inductor 318 illustrated in FIG. 9.

As the support frame 414 moves from the deployed configuration (FIGS. 10 and 12) to the collapsed configuration (FIG. 11), the center of the cloverleaf structure moves outward and distally as the cloverleaf structure 419 transitions from a shape that substantially extends radially from the longitudinal axis 90 (FIGS. 10 and 12) to a shape that substantially extends along the longitudinal axis 90 (FIG. 11). In the deployed configuration, the atraumatic structure 420 preferably covers a majority of the cloverleaf structure 419. In the collapsed configuration, the atraumatic structure 420 covers only distal tips of the cloverleaf structure 419.

The end effector 400 can be modified to include one or more inflatable members 130 (FIGS. 2, 6A, and 6B) coupled to one or more spines 410 approximate the distal end of the end effector 400 such that the inflatable member(s) 130 is/are configured to collapse for delivery through a sheath and is/are configured to inflate in a deployed configuration, and such that the inflatable member(s) in the deployed configuration prevent the distal end of the basket assembly 400 from contacting tissue. The inflatable members 130 may be sufficient to inhibit the cloverleaf structure 419 from impending on tissue or prevent the cloverleaf structure 419 from contacting tissue so that the atraumatic structure 420 can be omitted.

Alternatively, the support frame 414 can be modified to include one or more loop members 111, 112, 113 each having a pair of spines 111 and interlocking central regions at a central spine intersection 114 (FIGS. 2-5). The circular central portion 421 can be positioned distally over the central regions of the loop members to shield the distal end of the basket assembly from contacting tissue.

Having shown and described exemplary embodiments of the subject matter contained herein, further adaptations of the methods and systems described herein may be accomplished by appropriate modifications without departing from the scope of the claims. In addition, where methods and steps described above indicate certain events occurring in certain order, it is intended that certain steps do not have to be performed in the order described but, in any order, as long as the steps allow the embodiments to function for their intended purposes. Therefore, to the extent there are variations of the invention, which are within the spirit of the disclosure or equivalent to the inventions found in the claims, it is the intent that this patent will cover those variations as well. Some such modifications should be apparent to those skilled in the art. For instance, the examples, embodiments, geometrics, materials, dimensions, ratios, steps, and the like discussed above are illustrative. Accordingly, the claims should not be limited to the specific details of structure and operation set forth in the written description and drawings.

The following clauses list non-limiting embodiments of the disclosure:

Clause 1. An end effector of a medical probe, the end effector comprising: a plurality of spines extending along a longitudinal axis and configured to expand away from the longitudinal axis to form a basket shape; a first loop member comprising a first pair of spines of the plurality of spines and a first central region disposed approximate a distal end of the end effector; a second loop member comprising a second pair of spines of the plurality of spines and a second central region disposed approximate the distal end of the end effector, the second central region comprising a portion disposed over a distal surface of the first central region and at least one extension disposed under a proximal surface of the first central region; and one or more electrodes coupled to each spine of the plurality of spines.

Clause 2. The end effector of clause 1, further comprising: a third loop member comprising a third pair of spines of the plurality of spines and a third central region disposed approximate the distal end of the end effector, the third central region comprising a portion disposed over a distal surface of the second central region, at least one extension disposed under a proximal surface of the second central region, and at least one extension disposed under a proximal surface of the first central region.

Clause 3. The end effector of clause 1 or 2, further comprising: a plurality of loop members each comprising a central region such that the central regions of the plurality of loop members are stacked at a central spine intersection in an inner-to-outer order, and such that at least a portion of the central regions comprise one or more extensions configured to overlap another loop member of the plurality of loop members out of order from the inner-to-outer order.

Clause 4. The end effector of any one of clauses 1-3, wherein central regions of loop members of the end effector are configured to interlock to maintain connection between the loop members approximate the distal end of the end effector.

Clause 5. The end effector of any one of clauses 1-4, wherein ends of each of the loop members are coupled to a shaft of the end effector.

Clause 6. The end effector of any one of clauses 1-5, wherein each of the loop members are formed from a planar sheet.

Clause 7. The end effector of any one of clauses 1-6, wherein the first loop member further comprises a notch through which a portion of the second central region extends so that the notch engages an extension of the at least one extension of the second central region.

Clause 8. The end effector of any one of clauses 1-7, further comprising: an inflatable member coupled to a spine of the plurality of spines approximate the distal end of the end effector such that the inflatable member is configured to collapse for delivery through a sheath and is configured to inflate in a deployed configuration, and such that the inflatable member in the deployed configuration prevents a distal end of the basket shape of the plurality of spines from contacting tissue.

Clause 9. The end effector of any one of clauses 1-8, further comprising: a plurality of inflatable members each coupled to a respective spine of the plurality of spines approximate the distal end of the end effector such that the plurality of inflatable members are configured to collapse for delivery through a sheath and are configured to inflate in a deployed configuration, and such that the plurality of inflatable members in the deployed configuration prevent a distal end of the basket shape of the plurality of spines from contacting tissue.

Clause 10. An end effector of a medical probe, the end effector comprising: a plurality of spines extending along a longitudinal axis and configured to expand away from the longitudinal axis to form a basket shape; a plurality of inflatable members each coupled to a respective spine of the plurality of spines approximate a distal end of the end effector such that the plurality of inflatable members are configured to collapse for delivery through a sheath and are configured to inflate in a deployed configuration, and such that the plurality of inflatable members in the deployed configuration prevent a distal end of the basket shape of the plurality of spines from contacting tissue; and one or more electrodes coupled to each spine of the plurality of spines.

Clause 11. The end effector of clause 10, further comprising: a first loop member comprising a first pair of spines of the plurality of spines and a first central region disposed approximate a distal end of the end effector; and a second loop member comprising a second pair of spines of the plurality of spines and a second central region disposed approximate the distal end of the end effector, the second central region comprising a portion disposed over a distal surface of the first central region and at least one extension disposed under a proximal surface of the first central region.

Clause 12. The end effector of clause 10, further comprising: a first loop member comprising a first pair of spines of the plurality of spines and a distal spine hub disposed approximate a distal end of the end effector, the distal spine hub comprising a plurality of openings therethrough; a second loop member comprising a second pair of spines of the plurality of spines and a distal segment extending through at least one opening of the plurality of openings; and one or more electrodes coupled to each spine of the plurality of spines.

Clause 13. The end effector of clause 10, further comprising: a support frame movable between a delivery configuration and a basket configuration and comprising the plurality of spines and a cloverleaf structure disposed around the longitudinal axis, the plurality of spines forming the basket shape in the basket configuration, a distal spine portion of the plurality of spines defining the cloverleaf structure, the cloverleaf structure defining a central cutout with a central area disposed about the longitudinal axis, and the cloverleaf structure being aligned cylindrically about then longitudinal axis in the delivery configuration and angled radially from the longitudinal axis in the basket configuration; and an atraumatic structure covering a portion of the cloverleaf structure of the support frame and comprising a plurality of radial extensions each extending along a respective spine of the plurality of spines such that the radial extensions are configured to slide along the respective spine as the support frame moves between the delivery configuration and the basket configuration.

Clause 14. An end effector of a medical probe, the end effector comprising: a plurality of spines extending along a longitudinal axis and configured to expand away from the longitudinal axis to form a basket shape; a first loop member comprising a first pair of spines of the plurality of spines and a distal spine hub disposed approximate a distal end of the end effector, the distal spine hub comprising a plurality of openings therethrough; a second loop member comprising a second pair of spines of the plurality of spines and a distal segment extending through at least one opening of the plurality of openings; and one or more electrodes coupled to each spine of the plurality of spines.

Clause 15. The end effector of clause 14, wherein the first loop member is formed from a planar sheet cut to form the distal spine hub and the first pair of spines.

Clause 16. The end effector of clause 14 or 15, wherein the distal segment of the second loop member extends through two openings of the plurality of openings.

Clause 17. The end effector of any one of clauses 14-16, wherein the distal segment of the second loop member extends over a distal surface of the distal spine hub.

Clause 18. The end effector of any one of clauses 14-17, further comprising: an atraumatic cover over a distal surface of the distal spine hub and the distal segment of the second loop member.

Clause 19. The end effector of any one of clauses 14-18, further comprising: a third loop member comprising a third pair of spines of the plurality of spines and a distal segment extending through at least one opening of the plurality of openings.

Clause 20. The end effector of clause 19, wherein the distal segment of the third loop member is parallel to the distal segment of the second loop member.

Clause 21. The end effector of clause 19, wherein the distal segment of the third loop member overlaps the distal segment of the second loop member.

Clause 22. The end effector of any one of clauses 19-21, further comprising: a third loop member comprising a third pair of spines of the plurality of spines and a distal segment extending through at least one opening of the plurality of openings.

Clause 23. The end effector of clause 22, further comprising: a fourth loop member comprising a fourth pair of spines of the plurality of spines and a distal segment extending through at least one opening of the plurality of openings.

Clause 24. The end effector of any one of clauses 14-23, wherein ends of each of the loop members are coupled to a shaft of the end effector.

Clause 25. The end effector of any one of clauses 14-23, further comprising: an inflatable member coupled to a spine of the plurality of spines approximate the distal end of the end effector such that the inflatable member is configured to collapse for delivery through a sheath and is configured to inflate in a deployed configuration, and such that the inflatable member in the deployed configuration prevents a distal end of the basket shape of the plurality of spines from contacting tissue.

Clause 26. An end effector of a medical probe, the end effector comprising: a plurality of spines extending along a longitudinal axis and configured to expand away from the longitudinal axis to form a basket shape; a structural support member extending through a spine of the plurality of spines; a spiral inductor disposed approximate a distal end of the end effector, comprising a central axis along the longitudinal axis, and being electrically coupled to the structural support member so that the structural support member is configured to transmit electrical signals from the spiral inductor along the spine; and one or more electrodes coupled to each spine of the plurality of spines.

Clause 27. The end effector of clause 26, wherein the spiral inductor and the structural support member are formed from a singular sheet or singular tube.

Clause 28. The end effector of clause 26 or 27, wherein each of the one or more electrodes are electrically isolated from the spiral inductor.

Clause 29. The end effector of any one of clauses 26-28, further comprising: an inflatable member coupled to a spine of the plurality of spines approximate the distal end of the end effector such that the inflatable member is configured to collapse for delivery through a sheath and is configured to inflate in a deployed configuration, and such that the inflatable member in the deployed configuration prevents a distal end of the basket shape of the plurality of spines from contacting tissue.

Clause 30. An end effector of a medical probe, the end effector comprising: a plurality of spines; a support frame movable between a delivery configuration and a basket configuration and extending through the plurality of spines so that the plurality of spines are configured to self-expand away from a longitudinal axis from a proximal portion to a distal spine portion to form a basket shape in the basket configuration, a distal portion of the support frame defining a cloverleaf structure disposed around the longitudinal axis, the cloverleaf structure defining a central cutout with a central area disposed about the longitudinal axis, the cloverleaf structure being aligned cylindrically about the longitudinal axis in the delivery configuration and angled radially from the longitudinal axis in the basket configuration; an atraumatic structure covering a portion of the cloverleaf structure of the support frame and comprising a plurality of radial extensions each extending along a respective spine of the plurality of spines such that the radial extensions are configured to slide along the respective spine as the support frame moves between the delivery configuration and the basket configuration; and one or more electrodes coupled to each spine of the plurality of spines.

Clause 31. The end effector of clause 30, the atraumatic structure comprising a circular central portion covering a majority of the cloverleaf structure.

Clause 32. The end effector of clause 30 or 31, further comprising: an inflatable member coupled to a spine of the plurality of spines approximate a distal end of the end effector such that the inflatable member is configured to collapse for delivery through a sheath and is configured to inflate in a deployed configuration, and such that the inflatable member in the deployed configuration prevents a distal end of the basket shape of the plurality of spines from contacting tissue.

What is claimed is:

1. An end effector of a medical probe, the end effector comprising:

a plurality of spines extending along a longitudinal axis and configured to expand away from the longitudinal axis to form a basket shape;

a first loop member comprising a first pair of spines of the plurality of spines and a first central region disposed approximate a distal end of the end effector;

a second loop member comprising a second pair of spines of the plurality of spines and a second central region disposed approximate the distal end of the end effector, the second central region comprising a portion disposed over a distal surface of the first central region and at least one extension disposed under a proximal surface of the first central region;

a third loop member comprising a third pair of spines of the plurality of spines and a third central region disposed approximate the distal end of the end effector, the third central region comprising a portion disposed over a distal surface of the second central region, at least one extension disposed under a proximal surface of the second central region, and at least one extension disposed under a proximal surface of the first central region; and one or more electrodes coupled to each spine of the plurality of spines.

2. The end effector of claim 1, wherein the first central region, the second central region, and the third central region are configured to interlock to maintain connection between the first loop member, the second loop member, and the third loop member approximate the distal end of the end effector.

3. The end effector of claim 1, wherein ends of each of the first loop member, the second loop member, and the third loop member are coupled to a shaft of the end effector.

4. The end effector of claim 1, wherein each of the first loop member, the second loop member, and the third loop member are formed from a planar sheet.

5. The end effector of claim 1, wherein the first loop member further comprises a notch through which a portion of the second central region extends so that the notch engages an extension of the at least one extension of the second central region.

6. The end effector of claim 1, further comprising:

an inflatable member coupled to a spine of the plurality of spines approximate the distal end of the end effector such that the inflatable member is configured to collapse for delivery through a sheath and is configured to inflate in a deployed configuration, and such that the inflatable member in the deployed configuration prevents a distal end of the basket shape of the plurality of spines from contacting tissue.

7. The end effector of claim 1, further comprising:

a plurality of inflatable members each coupled to a respective spine of the plurality of spines approximate the distal end of the end effector such that the plurality of inflatable members are configured to collapse for delivery through a sheath and are configured to inflate in a deployed configuration, and such that the plurality of inflatable members in the deployed configuration prevent a distal end of the basket shape of the plurality of spines from contacting tissue.

8. An end effector of a medical probe, the end effector comprising:

a plurality of spines extending along a longitudinal axis and configured to expand away from the longitudinal axis to form a basket shape;

a first loop member comprising a first pair of spines of the plurality of spines and a first central region disposed approximate a distal end of the end effector;

a second loop member comprising a second pair of spines of the plurality of spines and a second central region disposed approximate the distal end of the end effector, the second central region comprising a portion disposed over a distal surface of the first central region and at least one extension disposed under a proximal surface of the first central region;

one or more electrodes coupled to each spine of the plurality of spines; and an inflatable member coupled to a spine of the plurality of spines approximate the distal end of the end effector such that the inflatable member is configured to collapse for delivery through a sheath and is configured to inflate in a deployed configuration, and such that the inflatable member in the deployed configuration prevents a distal end of the basket shape of the plurality of spines from contacting tissue.

9. The end effector of claim 8, further comprising:

a third loop member comprising a third pair of spines of the plurality of spines and a third central region disposed approximate the distal end of the end effector, the third central region comprising a portion disposed over a distal surface of the second central region, at least one extension disposed under a proximal surface of the second central region, and at least one extension disposed under a proximal surface of the first central region.

10. The end effector of claim 8, wherein the first central region and the second central region are configured to interlock to maintain connection between the first loop member and the second loop member approximate the distal end of the end effector.

11. The end effector of claim 8, wherein ends of each of the first loop member and the second loop member are coupled to a shaft of the end effector.

12. The end effector of claim 8, wherein each of the first loop member and the second loop member are formed from a planar sheet.

13. The end effector of claim 8, wherein the first loop member further comprises a notch through which a portion of the second central region extends so that the notch engages an extension of the at least one extension of the second central region.

14. An end effector of a medical probe, the end effector comprising:

a plurality of spines extending along a longitudinal axis and configured to expand away from the longitudinal axis to form a basket shape;

a first loop member comprising a first pair of spines of the plurality of spines and a first central region disposed approximate a distal end of the end effector;

a second loop member comprising a second pair of spines of the plurality of spines and a second central region disposed approximate the distal end of the end effector, the second central region comprising a portion disposed over a distal surface of the first central region and at least one extension disposed under a proximal surface of the first central region;

one or more electrodes coupled to each spine of the plurality of spines; and a plurality of inflatable members each coupled to a respective spine of the plurality of spines approximate the distal end of the end effector such that the plurality of inflatable members are configured to collapse for delivery through a sheath and are configured to inflate in a deployed configuration, and such that the plurality of inflatable members in the deployed configuration prevent a distal end of the basket shape of the plurality of spines from contacting tissue.

15. The end effector of claim 14, further comprising:

a third loop member comprising a third pair of spines of the plurality of spines and a third central region disposed approximate the distal end of the end effector, the third central region comprising a portion disposed over a distal surface of the second central region, at least one extension disposed under a proximal surface of the second central region, and at least one extension disposed under a proximal surface of the first central region.

16. The end effector of claim 14, wherein the first central region and the second central region are configured to interlock to maintain connection between the first loop member and the second loop member approximate the distal end of the end effector.

17. The end effector of claim 14, wherein ends of each of the first loop member and the second loop member are coupled to a shaft of the end effector.

18. The end effector of claim 14, wherein each of the first loop member and the second loop member are formed from a planar sheet.

19. The end effector of claim 14, wherein the first loop member further comprises a notch through which a portion of the second central region extends so that the notch engages an extension of the at least one extension of the second central region.

* * * * *